US008748129B2

(12) United States Patent
Nicaud et al.

(10) Patent No.: US 8,748,129 B2
(45) Date of Patent: Jun. 10, 2014

(54) METHOD FOR THE TARGETED INTEGRATION OF MULTIPLE COPIES OF A GENE OF INTEREST IN A YARROWIA STRAIN

(75) Inventors: Jean-Marc Nicaud, Trappes (FR); Franck Fudalej, Rueil-Malmaison (FR); Cécile Neuveglise, Auffargis (FR); Jean-Marie Beckerich, Bourg-la-Reine (FR)

(73) Assignee: Institut National de la Recherche Agronomique, Paris (FR)

(*) Notice: Subject to any disclaimer, the term of this patent is extended or adjusted under 35 U.S.C. 154(b) by 227 days.

(21) Appl. No.: 12/866,022

(22) PCT Filed: Feb. 5, 2009

(86) PCT No.: PCT/EP2009/051332

§ 371 (c)(1), (2), (4) Date: Oct. 1, 2010

(87) PCT Pub. No.: WO2009/098263

PCT Pub. Date: Aug. 13, 2009

(65) Prior Publication Data

US 2011/0053219 A1 Mar. 3, 2011
US 2012/0034652 A9 Feb. 9, 2012

(30) Foreign Application Priority Data

Feb. 5, 2008 (FR) ..................................... 08 50736

(51) Int. Cl.

| | |
|---|---|
| ***C12N 15/81*** | (2006.01) |
| ***C12N 1/19*** | (2006.01) |
| ***C12N 1/15*** | (2006.01) |
| ***C12P 21/00*** | (2006.01) |

(52) U.S. Cl.
USPC ..................... 435/69.1; 435/471; 435/254.11; 435/134; 435/243

(58) Field of Classification Search
None
See application file for complete search history.

(56) References Cited

U.S. PATENT DOCUMENTS

| | | | |
|---|---|---|---|
| 4,937,189 | A | 6/1990 | Davidow et al. |
| 4,959,317 | A | 9/1990 | Sauer |
| 5,965,444 | A | 10/1999 | Ashikari et al. |
| 6,083,717 | A | 7/2000 | Madzak et al. |
| 6,265,185 | B1 | 7/2001 | Muller et al. |
| 6,534,315 | B1 | 3/2003 | Bauer et al. |
| 6,582,951 | B1 | 6/2003 | Nicaud et al. |
| 2005/0130280 | A1 | 6/2005 | Pollak et al. |
| 2006/0057690 | A1 | 3/2006 | Xue et al. |
| 2006/0094192 | A1 | 5/2006 | Yang et al. |
| 2011/0183387 | A1 | 7/2011 | Nicauda et al. |

FOREIGN PATENT DOCUMENTS

| | | | |
|---|---|---|---|
| EP | 0 138 508 | A1 | 4/1985 |
| EP | 0 220 009 | A2 | 4/1987 |
| EP | 0 220 864 | | 5/1987 |
| EP | 0 635 574 | A1 | 1/1995 |
| EP | 0 814 165 | | 12/1997 |
| EP | 0 994 192 | | 4/2000 |
| WO | WO 96/41889 | | 12/1996 |
| WO | WO 00/12729 | | 3/2000 |
| WO | WO 01/83773 | | 11/2001 |
| WO | WO 2006/064131 | | 6/2006 |
| WO | WO 2010/004141 | A2 | 1/2010 |

OTHER PUBLICATIONS

Barth et al. (1996) "The dimorphic fungus *Yarrowia lipolytica*," In: *Non conventional yeasts in biotechnology* (Wolf, K., Ed.). Springer-Verlag, Berlin, p. 313-388.

Bordes et al. (Aug. 2007) "A New Recombinant Protein Expression System for High-Throughput Screening in the Yeast *Yarrowia lipolytica*." *J. Microbiological Methods* 70(3):493-502.

Fickers et al. (Dec. 2003) "New Disruption Cassettes for Rapid Gene Disruption and Marker Rescue in the Yeast *Yarrowia lipolytica*." *J. Microbiological Methods* 55(3):727-737.

Juretzek et al. (Jan. 2001) "Vectors for Gene Expression and Amplification in the Yeast *Yarrowia lipolytica*." *Yeast* 18(2):97-113.

Madzak et al. (Apr. 2004) "Heterologous Protein Expression and Secretion in the Non-Conventional Yeast *Yarrowia lipolytica*: A Review," *J. Biotechnology* 109(91- 92):63-81.

Madzak et al. (Web Release Nov. 20, 2004) "Heterologous Production of Laccase from the Basuduintcete *Pycnoporus cinnabarinus* in the Dimorphic Yeast *Yarrowia lipolytica*," *FEMS Yeast Research* 5:635-646.

Maftahi et al. (1996) "Sticky-End Polymerase Chain Reaction Method for Systematic Gene Disruption in *Saccharomyces cerevisiae*," *Yeast* 12:859-868.

(Continued)

*Primary Examiner* — Kagnew H Gebreyesus
(74) *Attorney, Agent, or Firm* — Lathrop & Gage LLP

(57) ABSTRACT

This invention concerns a method for the targeted integration of at least three copies of a gene of interest in the genome of a *Yarrowia* strain including the steps of: (a) cultivating a *Yarrowia* strain, said strain including a deletion among at least three genes, the phenotype associated with each of these deletions corresponding to an auxotrophy or to a dominant character for this strain; (b) transforming said *Yarrowia* strain thus obtained with at least three recombinant vectors that include selection markers allowing, for this strain, the complementation of auxotrophy and, potentially, of the dominant character resulting from each of these deletions; and (c) selecting, on a minimum medium, the yeasts having integrated said at least three recombinant vectors. This invention also includes a method for producing a polypeptide of interest using this method as well as a method for obtaining a modified *Yarrowia* strain including a deletion among at least three genes, the phenotype associated with each of these deletions corresponding to an auxotrophy or to a dominant character for this strain.

23 Claims, 8 Drawing Sheets

(56) References Cited

OTHER PUBLICATIONS

Figure 1:
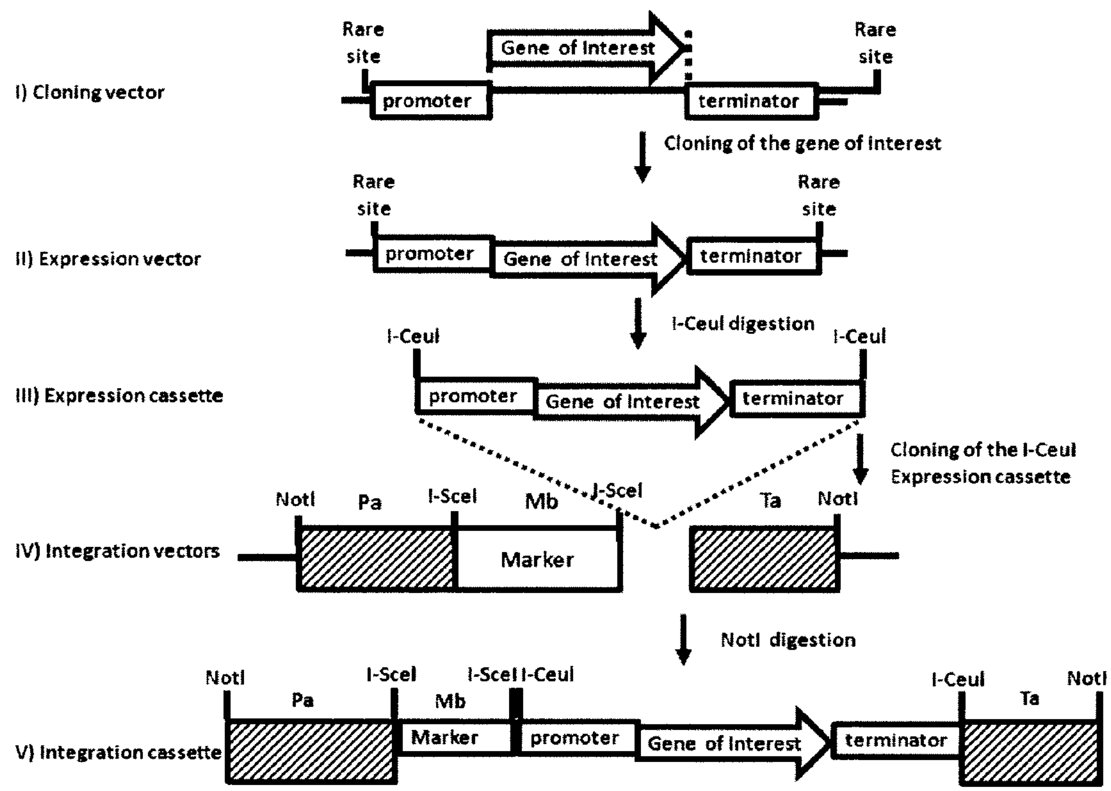

Wang et al. (1999) "Evaluation of Acyl CoA oxidase (Aox) Isozymes Function in the n-Alkanes-Assimilating *Yeast Yarrowia lipolytica*," *J. Bacteriol.*. 181:5140-5148.

International Search Report for International Application PCT/EP2009/051332 dated Apr. 27, 2009.

Control strains: FF-lug; FF-lua; FF-luga

METHOD FOR THE TARGETED INTEGRATION OF MULTIPLE COPIES OF A GENE OF INTEREST IN A YARROWIA STRAIN

CROSS-REFERENCE TO RELATED APPLICATIONS

This application is a U.S. National Stage of international application PCT/EP2009/051332, filed Feb. 5, 2009, which designates the U.S. and which was not filed or published in English and claims priority to French patent application FR 0850736, filed Feb. 5, 2008. Each of these applications is incorporated by reference herein in its entirety.

This invention concerns a method for the targeted integration of at least three copies of a gene of interest in the genome of a *Yarrowia* strain that includes the steps of (a) cultivating a *Yarrowia* strain, said strain including a deletion among at least three genes, the phenotype associated with each of said deletions corresponding to an auxotrophy or to a dominant character for said strain; (b) transforming the *Yarrowia* strain thus obtained using at least three recombinant vectors, including selection markers enabling, for this *Yarrowia* strain, the complementation of auxotrophy and, potentially, the dominant character resulting from each of the deletions; and (c) selecting, on a minimum medium, yeasts having integrated these at least three recombinant vectors. This invention also includes a method for producing a polypeptide of interest using said method as well as a method for obtaining a modified *Yarrowia* strain including a deletion among at least three genes, the phenotype associated with each of these deletions corresponding to an auxotrophy or to a dominant character for this strain.

*Yarrowia lipolytica* yeast is now increasingly used as expression host for genes of interest. This yeast has the specific characteristic of producing and secreting high molecular weight proteins such as alkaline proteases, acid proteases or RNase with great effectiveness in the culture medium, these proteins then being easily recovered from the culture medium. In order to permit the expression of these genes of interest, various technologies were developed early such as those described more particularly in patent EP 0 138 508 B1 or EP 0 220 864 B1. These different technologies have in common that they use "integrative" vectors that allow the insertion of a DNA segment carrying the gene of interest in the chromosomal DNA; this gene of interest is then expressed. Nevertheless, none of these technologies have completely satisfied the requirements of industrial production, namely a large yield and great stability over time.

New technologies have been developed to better satisfy these industrial requirements.

Thus, patent application PCT WO 00/12729 describes a technology that uses integrative vectors comprising a sequence of interest flanked by zeta sequences corresponding to the LTRs of the retrotransposon Ylt1 of *Yarrowia lipolytica*. When they are used in *Yarrowia lipolytica* strains devoid of zeta sequences, these integrative vectors allow multicopy, random integrations in the genome of these strains. This particular technology was used in particular to produce acid-resistant extracellular lipase LIP2 (see patent application PCT WO 01/83773).

However, it appeared that the majority of the *Yarrowia lipolytica* strains transformed by LIP2 had mediocre genetic stability, generally below 50%. Furthermore, since these transformed strains are obtained as a result of random integration events, monitoring the genetic stability of the strains via sequencing of the insertion sites is extremely tedious.

Added to the problems relating to the stability of the obtained strains and the difficulty in identifying the precise integration site of the exogenous sequence are the additional problems associated with the absence of *Yarrowia lipolytica* strains lacking multiple selection markers due to the instability of these strains.

Among the expression cassette integration methods, we can cite those using homologous transformation methods, but these methods use few markers (LEU2, URA3, LYS5) and few multimarked strains and have deletions allowing a sharp decrease in conversion rates. The strains often have genome markers corresponding to mutations and few markers corresponding to deletions. The only genome markers known with deletions are: ura3-302 (deletion of 695 pb), ura3-41 (deletion of 41 pb), leu2-270 (StuI deletion of 681 pb). MADZAK et al. (*J. of Biotech*., vol. 109, p: 63-81, 2004) thus describes the markers ura3-302 and leu2-270.

Among the vectors, we can cite those that allow targeted integration, but by integrating the plasmid portion, i.e., integration of plasmids in a pBR322 (Madzak et. al., Fems yeast research, vol. 5, p: 635-646, 2005) or zeta (Bordes et al., J. Microbiol Methods Vol. 70, p. 493-502, 2007) platform. There are autocloning vectors for integration and amplification. However these vectors are dispersed and random.

To produce therapeutic proteins, no plasmid DNA is necessary and targeted integration is necessary to identify the insertion and verify its sequence. It is also necessary to be able to increase the number of copies of the gene to increase expression.

The inventors have devised a method that allows targeted integration thanks to "integration vectors" that were constructed to release the integration cassette (rare site 1) and eliminate the vector portion, which have rare sites for introducing the selection markers quickly (rare site 2) and for cloning the expression cassettes (rare site 3). Combinations of integration vectors with a different locus/marker combination.

The inventors have also:

- optimized transformation conditions to increase the transformation rates, particularly for the ADE2 and GUT2 markers; and
- achieved the association of integration and a phenotype to quickly identify the interesting clones that have integrated the integration cassettes in the desired locus.

Thus, the inventors have produced here a method for integrating an expression cassette at a locus that makes it possible to introduce a new selection marker at the same time (e.g., new genome marker, new auxotrophy) to allow a new integration with a new integration cassette possessing the corresponding selection marker.

Due to the possibility of good transformation effectiveness, a low conversion rate, and insertion identification screening (lipase for LIP2, brown for ADE2, SUC− for URA3), it is thus possible to achieve cointegration (transforming with two integration cassettes). This makes it possible to reduce the time necessary to obtain the production strain. Likewise, insertion at defined sites allows rapid characterization of the production strains. The final strain being prototrophic The final strain no longer expresses the major proteins secreted (AEP protease, LIP2p lipase); it has stable deletions, weak cell lysis and a clean supernatant (few secreted proteins).

The inventors have also demonstrated the possibility of obtaining the general excision of the markers with these excisable markers making it possible to regenerate the markers and thus to be able once again to integrate new copies.

To obtain multi-marked strains, a genome marker can be inserted via different methods.

For example, the POP IN/POP OUT method is used in *Yarrowia lipolytica* to construct the leu2-270, ura3-302 and xpr2-322 markers and is described in the publication by G. Barth et al.: *Yarrowia lipolytica*. in: Nonconventional Yeasts in Biotechnology A Handbook (Wolf, K., Ed.), Vol. 1, 1996, pp. 313-388. Springer Verlag. It consists in integrating a vector possessing a deletion of the gene at the locus then in selecting the excision of this vector and identifying a clone that, through recombination, eliminated the wild-type gene and retained the mutated gene. This is a lengthy, inefficient method that also requires the use of a counter-selection marker. For example, the counter-selection of Ura+clones with 5FOA. This counter-selection can introduce secondary mutations.

The SEP method (Maftahi, N, Nicaud, J-M., Gaillardin, C., 1996. Sticky-end polymerase chain reaction method for systematic gene disruption in *Saccharomyces cerevisiae. Yeast*, vol. 12, p: 859-868) can also be used. This method was adapted in *Yarrowia lipolytica* for the successive disruption of the POX genes (Wang, H. J., Le Dall, M-T., Waché, Y., Belin, J-M., Gaillardin, C. Nicaud, J-M., 1999. Evaluation of Acyl CoA oxidase (Aox) isozymes function in the n-alkanes-assimilating yeast *Yarrowia lipolytica. J. Bacteriol*., vol. 181, p. 5140-5148). This method is faster, but still requires the use of a counter-selection marker.

It is also possible to use the SEP/cre method developed by Fickers et al., (Fickers, P., Le Dall, M. T., Gaillardin, C., Thonart, P., Nicaud, J-M., New disruption cassettes for rapid gene disruption and marker rescue in the yeast *Yarrowia lipolytica*. J. Microbiol. Methods vol. 55, p: 727-737, 2003). This is a fast method that does not require the use of a counter-selection marker. This method consists in 1) selecting the gene of interest that is to be deleted, 2) constructing a disruption cassette via PCR ("Polymerase Chain Reaction) or via cloning, 3) introducing a selection marker containing on both sides a recombination sequence (advantageously a loxP or loxR sequence or derivative) allowing a recombination between it for the elimination of the marker (advantageously a loxP type sequence that allows recombination under the action of the cre recombinase), 4) selecting the strains with the gene of interest deleted (transformation and selection of the transformants) and verifying the disruption, 5) transforming with a vector allowing the expression of the recombinase (advantageously the cre recombinase, which allows the recombination of the loxP/loxR sequences and the elimination of the marker), and 6) the isolation of a clone having the deletion of the gene of interest and having lost the recombinase expression plasmid. However, it is necessary to optimize the deletions and the markers in order to minimize the gene conversions during transformation.

It is clear from the preceding that there are no existing transformation technologies making it possible to integrate the sequence of a gene of interest specifically and stably in the genome of *Yarrowia lipolytica* in order to obtain a significant expression of this gene.

The inventors have now shown that the stability of the *Yarrowia* strains obtained by transformation was highly dependent on the number of integrated copies. Thus, a strain with 8 integrated copies of the LIP2 gene has 70% stability; this stability increases to 98% for 7 copies and to 100% for 6 copies.

Similarly, the inventors have succeeded in developing new, viable strains of *Yarrowia lipolytica* displaying auxotrophy and, potentially, a dominant character associated with at least three distinct selection markers chosen in particular from among the selection markers Ura3, Leu2, Lut 2 and Ade2. The viable strains developed also have broad deletions (Ura3-302, Leu2-270, Gut2-744 and Ade2-844), particularly with the new Gut2-744 and Ade2-844 deletions, which make it possible to considerably limit the frequency of gene conversion (cf. examples).

The use of these types of strains in integration methods, particularly targeted integration methods, makes it possible to obtain transformed strains containing multiple integrations of a gene of interest much more quickly and simply.

Finally, the inventors have succeeded in developing a new method for transforming strains of *Yarrowia lipolytica* making it possible to obtain stable transformed strains with an interesting production level of a polypeptide of interest.

PURPOSE OF THE INVENTION

The purpose of the invention is to remedy the disadvantages of the prior art and quickly obtain strains that overproduce a gene or genes of interest for the production of heterologous proteins and to be able to quickly verify the expression cassettes and characterize the production strain.

Strains possessing selection markers allowing a low conversion level and high transformation effectiveness are used as microorganisms.

A set of vectors allowing the construction of vectors containing the expression cassettes and of vectors containing the integration cassettes are used;

Quick methods for identifying the transformants containing the integration of the integration cassettes at the defined loci are also used.

Finally, the method according to the invention allows the production of a heterologous protein.

In more detailed fashion, the invention proposes sets of strains, vectors, selection markers, and phenotype and characterization assays for the insertion of insertion cassettes to quickly obtain strains that overproduce a gene or genes of interest for the production of heterologous proteins and for the quick verification of the expression cassettes and characterization of the production strain that includes:

(a) Receiver strains containing deletions of genes conferring an auxotrophy or a growth defect on certain media;

(b) A set of cloning vectors allowing the construction of "expression vectors" that contain the expression cassettes; a set of "integration vectors" allowing the construction of integration vectors;

(c) Methods for obtaining transformants and for identifying the transformants containing the integration of the integration cassettes at the defined locus; and (d) A method for producing the heterologous protein.

As a result, the first purpose of the invention concerns a method for the targeted integration of at least three copies of a gene of interest in the genome of a *Yarrowia* strain including the steps of: 2 a deletion in at least three genes and characterized in that it is independent of any of these three genes; the phenotype associated with each of these deletions corresponds to an auxotrophy or to a dominant character for this strain;

b) transformation of this auxotrophic or dominant character *Yarrowia* strain with at least three recombinant vectors that contain selection markers enabling, for this *Yarrowia* strain, the complementation of the auxotrophy and/or the dominant phenotype resulting from each of the deletions, these recombinant vectors each containing:

i) the sequence of the gene of interest, ii) a selection marker, and iii) two DNA sequences framing the sequence of the gene of interest and the selection marker; these two DNA sequences are homologous to the sequences corresponding to the ends of the targeted integration site in the genome of the *Yarrowia* strain in order to allow the targeted integration of this recombinant vector via homologous recombination;

c) selection on a minimum medium of the yeasts having integrated at least three recombinant vectors.

In a preferred embodiment, the targeted integration method according to the invention is characterized in that the genes having a deletion and associated with an auxotrophic phenotype or a dominant character phenotype are chosen from among:

for the auxotrophy markers, the URA3, LEU2, GUT2, ADE2, HIS and LYS5 genes; and for the dominant characters, the hygromycin-resistance gene HYG4, and the MDR3, KanMX, HPH and Tn5ble genes.

Preferably, the genes with a deletion are associated with an auxotrophic phenotype, UFA3, LEU2, GUT2 and ADE2 genes being the most preferred genes.

Advantageously, the URA3 deletion corresponds to the Ura3-302 deletion, which is well known to the person skilled in the art and described in particular in MADZAK et al. (2004).

Advantageously, the LEU2 deletion corresponds to the Leu2-270 deletion also well known to one with ordinary skill in the art and described in particular in MADZAK et al. (2004).

Advantageously, the GUT2 deletion corresponds to the Gut2-744 deletion described in the examples. Gut2-744 corresponds to a complete deletion of the ORF of the GUT 2 gene (SEQ ID NO: 4), of which deletion is present in the mutant FF-Lug (CNCM-3911) and FF-luga (CNCM-3913) strains. After excision, the sequence SEQ ID NO: 11 remains on the *Yarrowia* genome between the GUT2 promoter and terminator sequences.

Advantageously, the ADE2 deletion corresponds to the Ade2-844 deletion described in the examples. Ade2-844 corresponds to a complete deletion of the ORF of the ADE2 gene (SEQ ID NO: 3), of which deletion is present in the FF-Lua (CNCM-3912) and FF-luga (CNCM -3913) strains. After excision, the sequence SEQ ID NO: 12 remains on the *Yarrowia* genome between the ADE2 promoter and terminator sequences.

Minimal medium, as used here, means a medium that does not contain the elements for which the *Yarrowia* strain is auxotrophic or one potentially allowing for the selection of the strain.

*Yarrowia* strains are well known to the one with ordinary skill in the art. We can cite the *Yarrowia lipolytica* strains as preferred examples of these strains.

The technique for transforming a yeast via targeted integration of a gene is a frequently used molecular biology technique. In this technique, a DNA fragment is cloned in a vector and inserted in the cell to be transformed; this DNA fragment is then integrated through homologous recombination in a targeted region of the receiver genome (ORR-WEAVER et al., *Proc. Natl. Acad. Sci. USA, vol.* 78, p: 6354-6358, 1981). These transformation methods are well known to one with ordinary skill in the art and are described in particular in ITO et al. (*J. Bacteriol*., vol. 153, p: 163-168, 1983), in KLEBE et al., (*Gene*, vol. 25, p: 333-341, 1983) and in GYSLER et al. (*Biotechn. Techn*., vol. 4, p: 285-290, 1990). Inasmuch as this recombination event is rare, selection markers are inserted between the sequences ensuring recombination in order to make it possible, after transformation, to isolate the cells where the integration of the fragment took place through the revelation of the corresponding markers.

The selection markers allowing auxotrophy complementation, also commonly called auxotrophic markers, are well known to one with ordinary skill in the art.

The selection marker URA3 is well known to one with ordinary skill in the art. More specifically, a *Yarrowia* strain whose URA3 gene (SEQ ID No. 1 for *Yarrowia lipolytica*, this sequence is also accessible via the accession number Yali0E2679g, encoding for orotidine-5'-phosphate decarboxylase, is inactivated (for example, by deletion) and will not be able to grow on a medium that is not supplemented with uracil. The integration of the URA3 selection marker in this strain of *Yarrowia* will then make it possible to restore the growth of this strain on a medium devoid of uracil.

The LEU2 selection marker described more particularly in U.S. Pat. No. 4,937,189 is also well known to the one with ordinary skill in the art. More specifically, a *Yarrowia* strain whose LEU2 gene (Yali0E26719g; SEQ ID No. 2 for *Yarrowia lipolytica*), encoding for 13-isopropylmalate dehydrogenase, is inactivated (for example by deletion) will not be able to grow on a medium not supplemented with leucine. As before, the integration of the LEU2 selection marker in this strain of *Yarrowia* will thus make it possible to restore the growth of this strain on a medium not supplemented with leucine.

The ADE2 selection marker is also well known to the one with ordinary skill in the field of yeast transformation. A *Yarrowia* strain whose ADE2 gene (SEQ ID No. 3 for *Yarrowia lipolytica*, YALI0B23188g), encoding for phosphoribosylaminoimidazole carboxylase, is inactivated (for example by deletion) will not be able to grow on a medium not supplemented with adenine. Here again, the integration of the ADE2 selection marker in this strain of *Yarrowia* will then make it possible to restore the growth of this strain on a medium not supplemented with adenine.

The GUT2 gene encodes for glycerol-3-phosphate dehydrogenase (SEQ ID No. 4, for *Yarrowia lipolytica*, YALI0B13970g) and its inactivation (for example by deletion) leads to the inability of the resulting mutant to grow on a non-fermentable medium whose carbon source corresponds to glycerol.

Among the resistance genes that may be used as a selection marker to give the *Yarrowia* strain a phenotype having a dominant character, we can cite:

The mouse MDR3 gene encodes for P-glycoprotein and, when it is expressed in a strain of *Yarrowia*, confers resistance to FK520 (antifungal agent and immunosuppressor; RAYMOND et al., *Mol. Cell. Biol*., vol. 14, p: 277-286, 1994).

The KanMX module, which contains the kan$^r$ sequence coming from the transposon Tn903 of *Escherichia coli* fused with the transcriptional sequences of the TEF gene of the filamentous fungus *Ashbya gossypii* or with any functional transcription promoter or terminator gives a *Yarrowia* strain resistance to geneticin (G418; WACH et al., *Yeast*, vol. 10, p: 1793-1808, 1994).

The HPH gene (HYG), originally from an *Escherichia coli* plasmid, allows resistance to hygromycin B (GRITZ & DAVIES, *Yeast*, vol. 8, p: 667-668, 1992; CORDERO OTERO & GAILLAIRDIN, *Applied Microbiol and Biotechnologies*, vol. 46, p: 143-148, 2004).

The *Escherichia coli* Tn5ble gene allows transformed yeast to acquire resistance to phleomycin (WENZEL et al., *Yeast*, vol. 8, p: 667-668, 1992).

Other selection markers that can be used in the method according to the invention are also described by BARTH & GAILLARDIN (*The dimoorphic fungus Yarrowia lipolytica. In: Non conventional yeasts in biotechnology* (Wolf K, Ed.). Springer-Verlag, Berlin, p: 313-388, 1996).

In an embodiment that is also preferred, the targeted integration method according to the invention is characterized in that in step b), the targeted integration site in the genome of this strain of *Yarrowia* is chosen from among the URA3, LEU2, ADE2, LIP2, LIP7, LIP8, AXP, GUT2 and XPR2 genes.

Preferably, the targeted integration method is characterized in that in step b), the integration site in the genome of this *Yarrowia* strain is chosen from among the genes, therefore the disruption confers an easily detectable phenotype (visualizable, measurable) particularly from among the URA3, ADE2, LIP2, LIP8 and AXP genes.

The LIP2 gene (SEQ ID NO. 5 for *Yarrowia lipolytica*) may be used as insertion locus. The LIP2 gene encodes for an extracellular lipase (PIGNEDE et al., *J. Bacteriol*., vol. 182 (10), p: 2802-10, 2000) which preferentially hydrolyzes the long chain triglycerides of the oleic residues. A *Yarrowia* strain whose LIP2 gene is inactivated (for example by deletion), will have reduced lipase activity (weak extracellular lipase activity, weak hydrolysis halo in a Petri dish of tributyrin).

The LIP8 gene (SEQ ID No. 6 for *Yarrowia lipolytica*) may be used as insertion locus. The LIP8 gene encodes for a triaclyglycerol hydrolase. A *Yarrowia* strain whose LIP8 gene is inactivated (after having inactivated LIP2) will not show any tributyrin hydrolysis halo on a dish of YNBT medium and no lipase activity (FICKERS et al., Fungal Genetics and Biology, vol. 42, P; 264-274, 2005).

The AXP gene (SEQ ID No. 7 for *Yarrowia lipolytica*) may be used as insertion locus. The AXP gene encodes for an extracellular acid protease normally expressed when the pH of the medium is lower than 4. A *Yarrowia* strain whose AXP gene is inactivated (for example by deletion) will present on a dish of YNBcaseine at an acid pH a diminished caseine hydrolysis halo and reduced protease activity (GLOVER et al., *Microbiology*, vol. 143, p: 3045-54, 1997).

The XPR2 gene encodes for an extracellular alkaline protease expressed when the pH of the medium is higher than 6. A *Yarrowia* strain whose XPR2 gene (SEQ ID No. 8 for *Yarrowia lipolytica*) is inactivated (for example by deletion) will show a reduced caseine hydrolysis halo and reduced protease activity on a dish of YNBcaseine at pH6 (DAVIDOW et. al., *J. Bacteriol*., vol. 169, p. 4621-9, 1987).

Preferably, this auxotrophic *Yarrowia* strain will include at least one deletion among the URA3, LEU2 and ADE2 or URA3, LEU2 and GUT2 genes.

For example, we can cite the strain of *Yarrowia lipolytica* deposited on Feb. 4, 2008 in accordance with the Budapest Treaty with the Collection nationale de Culture de Microorganismes (CNCM), PASTEUR INSTITUTE, 25 rue du Docteur Roux, 75724 PARIS CEDEX 15, France under the number CNCM-3912.

For example, we can cite the strain of *Yarrowia lipolytica* deposited on Feb. 4, 2008 in accordance with the Budapest Treaty with the Collection nationale de Culture de Microorganismes (CNCM), PASTEUR INSTITUTE, 25 rue du Docteur Roux, 75724 PARIS CEDEX 15, France under the number CNCM-3911.

Advantageously, the auxotrophic *Yarrowia* strain used in step a) in the method according to the invention includes a deletion among four genes resulting in an auxotrophic phenotype for the four genes of the group including URA3, LEU2, ADE2 and GUT2.

[Text illegible] the *Yarrowia lipolytica* strain deposited on Feb. 4, 2008, in accordance with the Budapest Treaty with the Collection nationale de Culture de Microorganismes (CNCM), PASTEUR INSTITUTE, 25 rue du Docteur Roux, 75724 PARIS CEDEX 15, France under the number CNCM-3913.

According to a preferred embodiment of the method according to the invention, this embodiment allows the targeted integration of from 3 to 10 copies of the gene of interest, preferably from 4 to 8 copies and more preferably still from 5 to 7 copies of this gene of interest.

Advantageously, the method according to the invention includes the transformation of this auxotrophic *Yarrowia* strain with from three to ten recombinant vectors, preferably from 4 to 8 recombinant vectors and, more preferably still, from 5 to 7 recombinant vectors.

The recombinant vectors used in step b) may also include one or more selection markers distinct from those allowing for this *Yarrowia* strain complementation of the auxotrophy and, potentially, of the dominant character resulting from the deletions among the at least three genes.

The encoding sequences for the selection marker and those for the gene of interest also include the elements necessary for their expression in a strain of *Yarrowia.*

These elements correspond in particular to active promoter and terminator sequences in a strain of *Yarrowia*. Preferably, the promoter and terminator sequences used belong to different genes in order to minimize the risks of undesired recombination in the genome of the *Yarrowia* strain.

These promoter sequences are well known to one with ordinary skill in the art and may correspond in particular to inducible or constitutive promoters. For examples of promoters that may be used in the method according to the invention, we can cite in particular the promoter of a gene of *Yarrowia lipolytica* that is strongly repressed by glucose and that is inducible by fatty acids or triglycerides such as the POX2 promoter of the acyl CoA oxidase 2 gene of *Yarrowia lipolytica* and the promoter of the LIP2 gene described in patent application PCT WO 01/83773. We can also use the promoter of the FBA1 gene of the fructose-bisphosphate aldolase gene (US 2005/0130280), the promoter of the YAT1 gene of the ammonium transporter gene (US 2006/0094102 A1), the promoter of the GPAT gene of the glycerol-3-phosphate O -acyltransferase gene (US 2006/0057690 A1), the TEF gene promoter (US 2001/6265185) and the hp4d hybrid promoter (WO9641889).

These terminator sequences are also well known to one with ordinary skill in the art, and we can cite as examples of terminator sequences that can be used in the method according to the invention the terminator sequence of the PGK1 gene and the terminator sequence of the LIP2 gene described in application PCT WO 01/83773.

When the product of the gene of interest is intended to be secreted by the host cell, this insert also includes secretion control signals for this product. To this end, functional signal sequences in *Yarrowia* strains can be used, for example all or part of the prepro sequence of the LIP2 gene described in application PCT WO 01/83773.

The gene of interest encodes for a polypeptide to be produced in large quantity in the transformed *Yarrowia* strain. This polypeptide preferably corresponds to a heterologous polypeptide like *Erwinia chrysanthemi* L-asparaginase (SEQ ID No. 9) or *Escherichia coli* (SEQ ID No. 10), however it may also correspond to an autologous peptide like the *Yarrowia lipolytica* LIP2 lipase described earlier.

According to a particular embodiment of the method according to the invention, steps b) transformation of the *Yarrowia* strain and c) selection on minimum medium are performed separately for each of the at least three recombinant vectors.

According to a more preferred embodiment, the targeted integration method according to the invention is characterized in that, in step b), transformations with at least three recombinant vectors are carried out independently and successively with each of the recombinant vectors or simultaneously with all of these recombinant vectors, and in that all of these transformations are followed by a step c) involving selection on a minimal medium of yeasts that have integrated all of these recombinant vectors.

According to another preferred embodiment, the method according to the invention is characterized in that the selection marker is framed by sequences allowing its excision to follow the targeted integration of this recombinant vector.

According to a fourth preferred embodiment of the method according to the invention, the selection marker is framed by sequences allowing its excision following the targeted integration of this recombinant vector.

The method according to the invention thus makes it possible to reuse a same selection marker, particularly an auxotrophic marker, for another targeted integration during a new transformation step.

Such sequences allowing the excision and elimination of a framed sequence in a *Yarrowia* strain are well known to one with ordinary skill in the art.

For example, we can cite the use of two identical or similar sequences, called direct repeat sequences (DRS), in order to obtain a recombination event as described in patent EP 0994192 B1 or in patent EP 0635574 B1.

For example, we can also cite the "Cre-lox" system as described in patent EP 0220009 B1, in which the sequences equivalent to the direct repeat sequences are in this case specific sequences called "lox," and the excision of the DNA sequence included between the two "lox" sequences is done in the presence of a "Cre" recombinase expressed by an expression vector. Other equivalent systems using other specific recombinases are also known to one of ordinary skill in the art, particularly the method described in patent EP 0814165 B1.

From another perspective, this invention concerns a method for producing a polypeptide encoded by a gene of interest, characterized in that it includes:

A) a targeted integration method according to the invention;

B) a step d) cultivation of the *Yarrowia* strain in a liquid culture medium containing assimilable sources of carbon, nitrogen and inorganic salts in order to allow the growth of this transformed strain of *Yarrowia* and C) the recovery of this expressed polypeptide of interest from the *Yarrowia* cells or from the culture medium obtained in step B).

Advantageously, the method according to the invention includes a step e) after step C) involving purification of this polypeptide encoded by the gene of interest.

This purification step e) can be performed either after cell lysis or, advantageously, using the culture medium in which it is secreted by the cells, using standard known techniques, for example by fractionated precipitation followed by one or more chromatography steps.

The transformed *Yarrowia* cells likely to be obtained via the method according to the invention are also part of this invention.

In another aspect, this invention relates to a method for obtaining a modified strain of *Yarrowia*, characterized in that it includes a step in which this *Yarrowia* strain is transformed with at least three vectors resulting in a *Yarrowia* strain including a deletion in at least three genes and characterized by the independence of these three genes from one another. The phenotype associated with each of these deletions corresponds to an auxotrophy or to a dominant character for this strain.

Preferably here, the deletion of at least three genes is associated with an auxotrophic or dominant character phenotype which are selected from among:

- for auxotrophic markers, the URA3, LEU2, GUT2, ADE2, HIS and LYS5 genes, and preferably from among the URA3, LEU2, GUT2 and ADE2 genes; and
- for dominant characters, the hygromycin-resistance gene HPH (HYG), and the MDR3, KanMX and Tn5ble genes, the HYG gene also being the most preferred of the resistance genes.

In an embodiment that is also preferred, the method for obtaining a modified *Yarrowia* strain according to the invention is characterized in that the genes having a deletion are associated with an auxotrophic phenotype and are preferably chosen from among the URA3, LEU2, GUT2 and ADE2 genes.

According to a final aspect, this invention concerns an auxotrophic strain of *Yarrowia* potentially having an acquired dominant character likely to be obtained via the method for obtaining a modified *Yarrowia* strain according to the invention. The strain includes a deletion in at least three genes of its genome and is characterized in the independence of these three genes from one another; the phenotype associated with each of these deletions corresponds to an auxotrophy or to a dominant character for this strain. Each of the preferences defined for the number of genes deleted, the genes chosen for the deletion as defined for step a) of the integration method according to the invention is also preferred for this method.

Advantageously, the strain of *Yarrowia* obtained via this method is a strain of *Yarrowia lipolytica.*

Preferably, this auxotrophic strain of *Yarrowia* will include at least one mutation among the URA3, LEU2 and ADE2 or URA3, LEU2 and GUT2 genes.

For example, we can cite the *Yarrowia lipolytica* strains deposited on Feb. 4, 2008 in accordance with the Budapest Treaty with the Collection nationale de Culture de Microorganismes (CNCM), PASTEUR INSTITUTE, 25 rue du Docteur Roux, 75724 PARIS CEDEX 15, France under the numbers CNCMI-3911 and CNCM I-3912.

According to a second preferred embodiment, the auxotrophic strain of *Yarrowia* used in the method according to the invention includes a mutation among four genes necessary for the growth of this strain, of which three genes are chosen from the group containing URA3, LEU2, ADE2, LIP2, LIP7, LIP8, AXP, GUT2 and XPR2.

Preferably, this auxotrophic strain of *Yarrowia* will include at least one mutation among the URA3, LEU2, ADE2 and GUT2 genes.

For example, we can cite the *Yarrowia lipolytica* strain deposited on Feb. 4, 2008 in accordance with the Budapest Treaty with the Collection nationale de Culture de Microorganismes (CNCM), PASTEUR INSTITUTE, 25 rue du Docteur Roux, 75724 PARIS CEDEX 15, France under the number CNCM I-3913.

This invention will be better understood by means of the figures and their legend and the additional description that will follow, which refers to non-limiting examples for obtaining transformed strains of *Yarrowia lipolytica* according to the invention.

FIGURE LEGENDS

FIG. 1: Schematic representation of the construction of a targeted "integration cassette" of an "expression cassette." 1) The gene of interest is cloned in an expression vector, 2) the expression cassette is released via I-SceI digestion, 3) then cloned in different integration vectors, 4) the integration cassettes are released via NotI digestion, purified and used to transform an integration strain.

Figure 2:
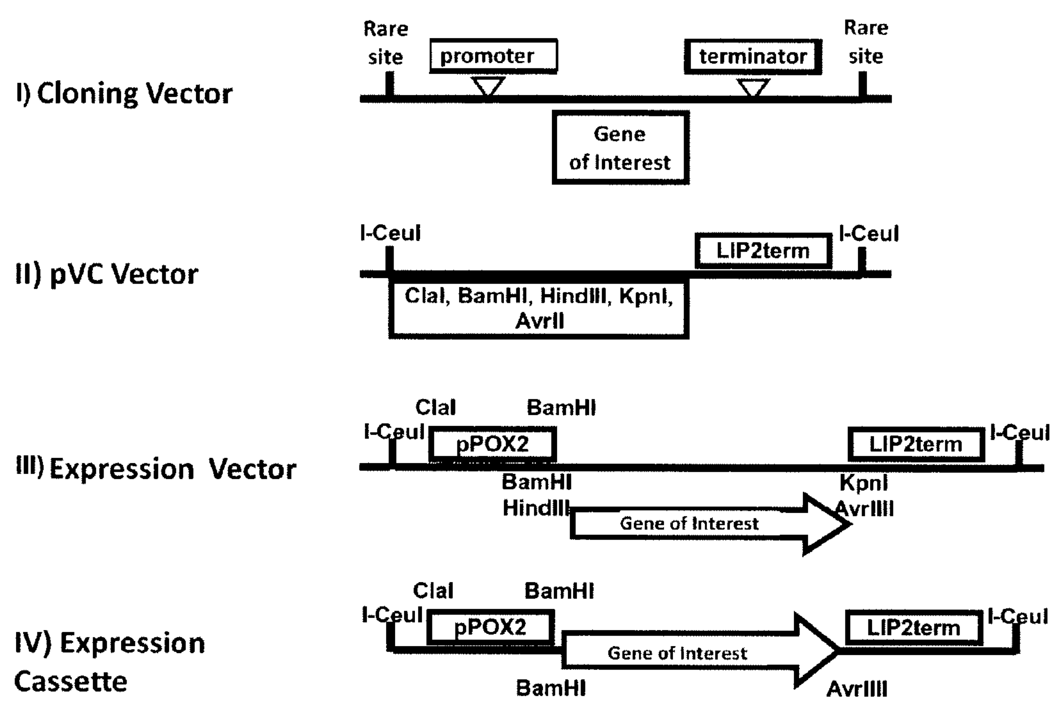

FIG. 2: Schematic representation of the cloning vector. 1) The cloning vector includes a strong promoter followed by unique restriction sites for the cloning of the gene of interest, a transcription terminator and on either site a rare site to allow the excision of the expression cassette. 2) the base pVC vector contains a multisite composed of the ClaI, BamHI, KpnI and AvrII sites, the terminator sequence of the LIP2 gene (LIP2term) with on either side the rare site I-CeuI, 3) the expression vector contains the pPOX2 promoter cloned at the ClaI and BamHI sites, 4) The expression cassette is obtained by multiple site cloning of the gene of interest, for example BamHI-AvrII, then digestion of the expression vector by I-CeuI.

Figure 3:
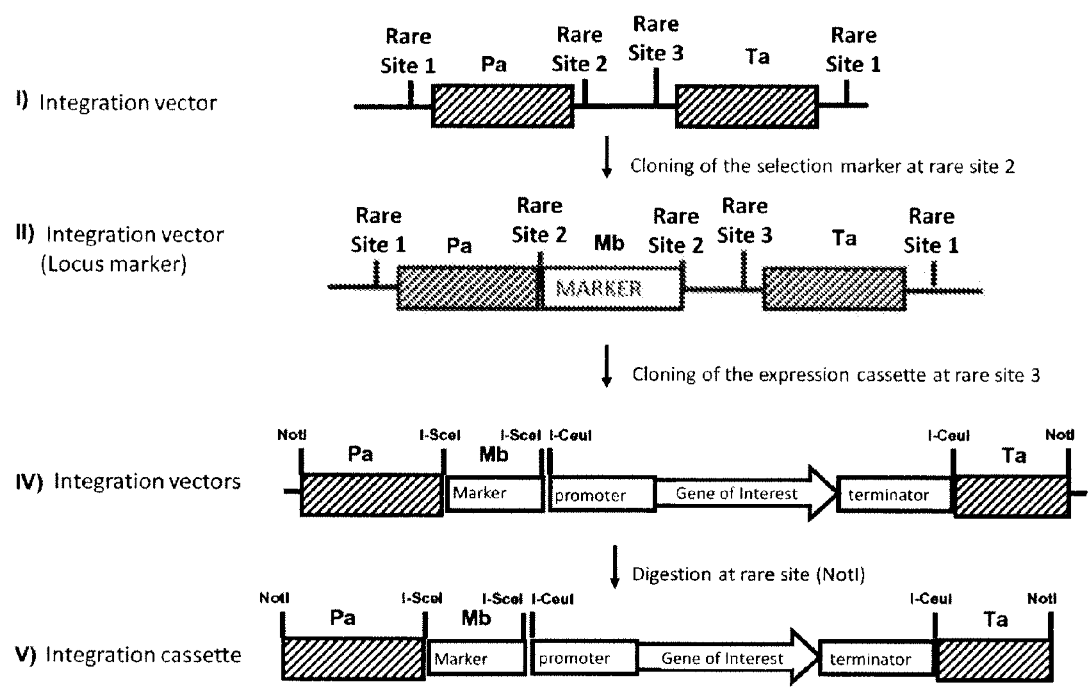

FIG. 3: Schematic representation of the integration vector and obtaining the targeted integration cassette. 1) The integration vector contains a region upstream of the insertion locus (region P, for promoter) and a region downstream of the insertion locus (region T for terminator) with on either side a rare site 1 for the excision of the integration cassette. Between P and T regions are two rare sites, rare site 2 for the insertion of the selection marker and rare site 3 for the insertion of the expression cassette.

Figure 4:
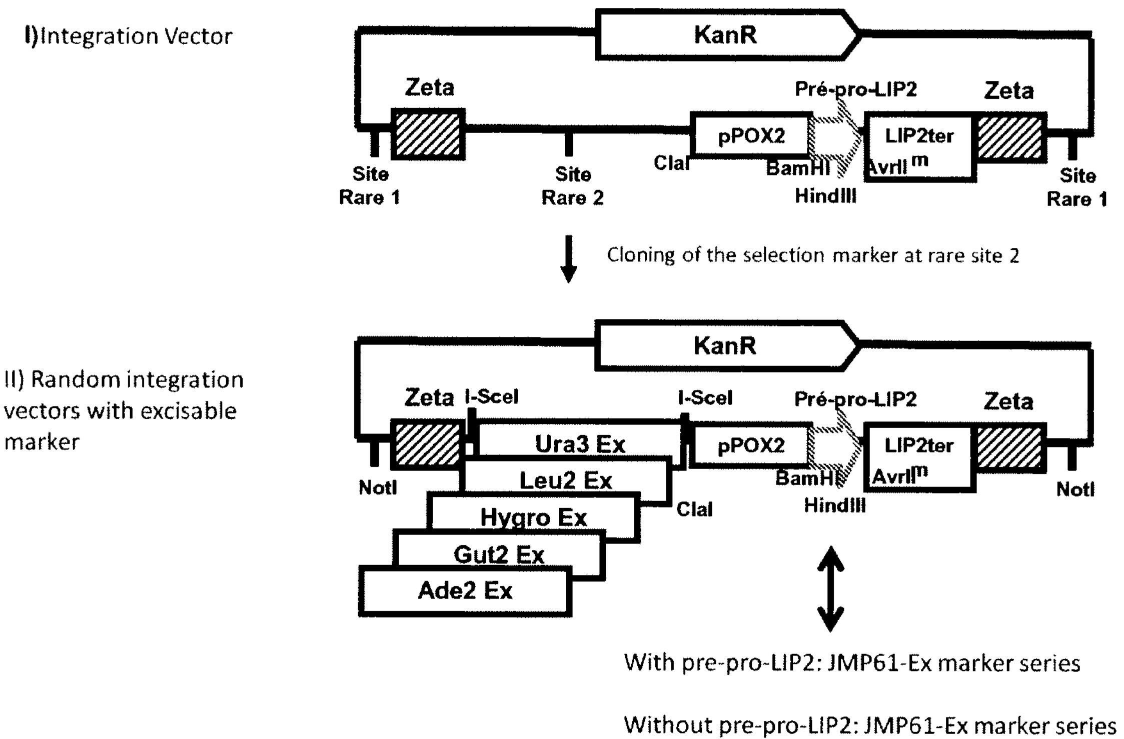

FIG. 4: Schematic representation of the integration vectors for random integration. I) schematic representation of the vector that includes a rare site I usable for releasing the expression cassette from the plasmid part, a rare site 2 for cloning the selection marker for *Y. lipolytica*. It contains a promoter between the ClaI and BamHI sites (here the pPOX2 promoter), the terminator of the LIP2 gene and the Zeta regions for random integration (see amplification patent). The JMP61 series has the addressing sequence of the Lip2 lipase. II) Schematic representation of the integration vectors for random integration constructed with the NotI site as rare site 1 and the I-SceI site as rare site 2 used for the insertion of the URA3, LEU2, Hyg, GUT2 and ADE2 markers.

Figure 5:
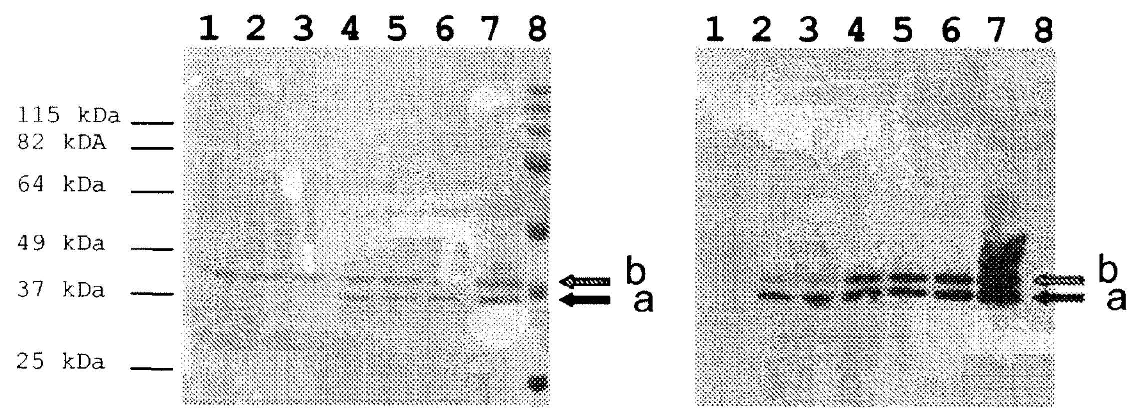

FIG. 5: Expression of the asparaginase in the strains containing different number of copies of the gene. A) Analysis on 10% NuPAGE electrophoresis gel and staining with colloidal blue (equivalent to 30 μl of supernatant), B) Analysis on 10% NuPAGE electrophoresis gel, transfer and detection by Western blot with an anti-Asparaginase antibody (equivalent to 10 μl of supernatant). Band a corresponds to the nonglycosylated protein and band b corresponds to the monoglycosylated protein. L1, receiving strain FF-luga; L2, strain 5LAsp1: ade2::GUT2-Asp, 1 copy; L3, strain 6LAsp1:ade2::GUT2-Asp, 1 copy; L4, strain 15LAsp2:ade2::GUT2-Asp lip2::URA3-Asp, 2 copies; L5 strain 21LAsp2:ade2::GUT2-Asp lip2::URA3-Asp:2 copies; L6, strain 1LAsp3:ade2::GUT2-Asp lip2::URA3-Asp leu2::ADE2-Asp:3 copies; L7, strain 2LAsp4:ade2::GUT2-Asp lip2::URA3-Asp leu2::ADE2-Asp ura3::Leu2-Asp:4 copies.

Figure 6:
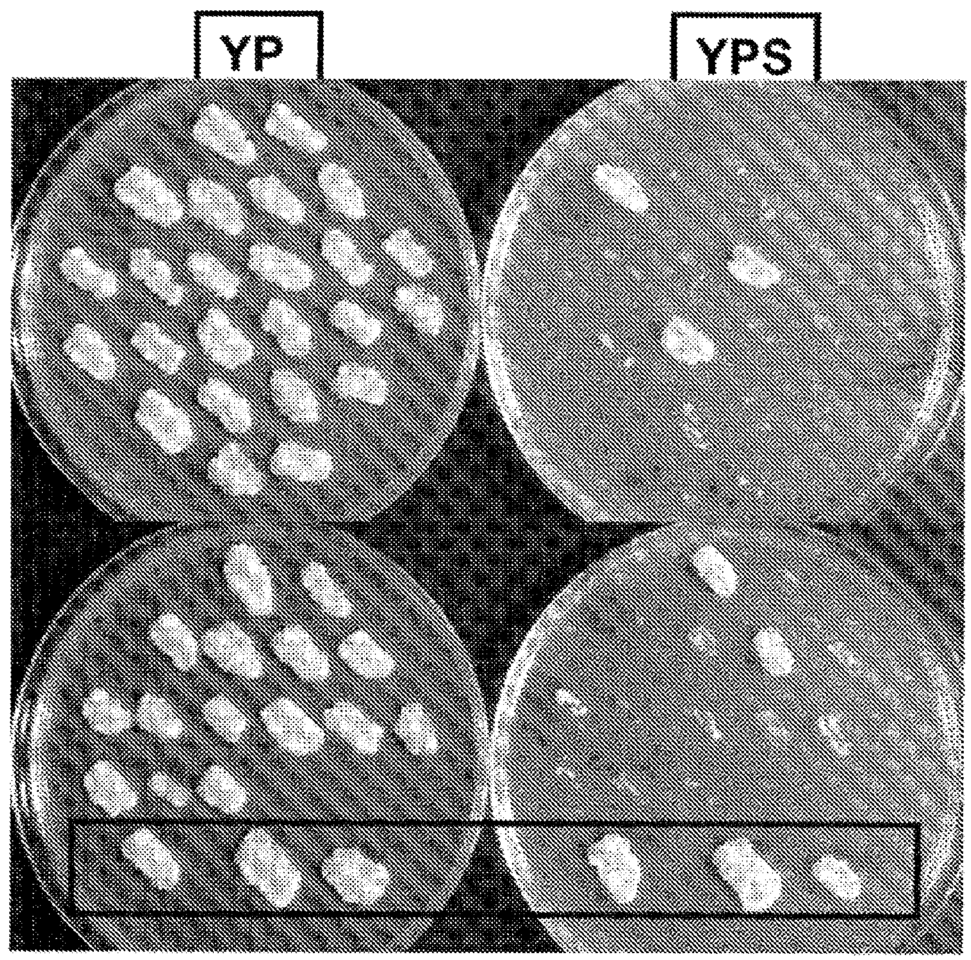

FIG. 6: Suc+/Suc− phenotype analysis to verify the insertion at the URA3 locus. The transformants obtained with the targeted integration cassette in the URA3 locus are streak tested on a dish of glucose-rich (YPD) and saccharose (YPS) medium. The receiver strains Suc+ FF-lug, FF-lua and FF-luga are used as control.

Figure 7:
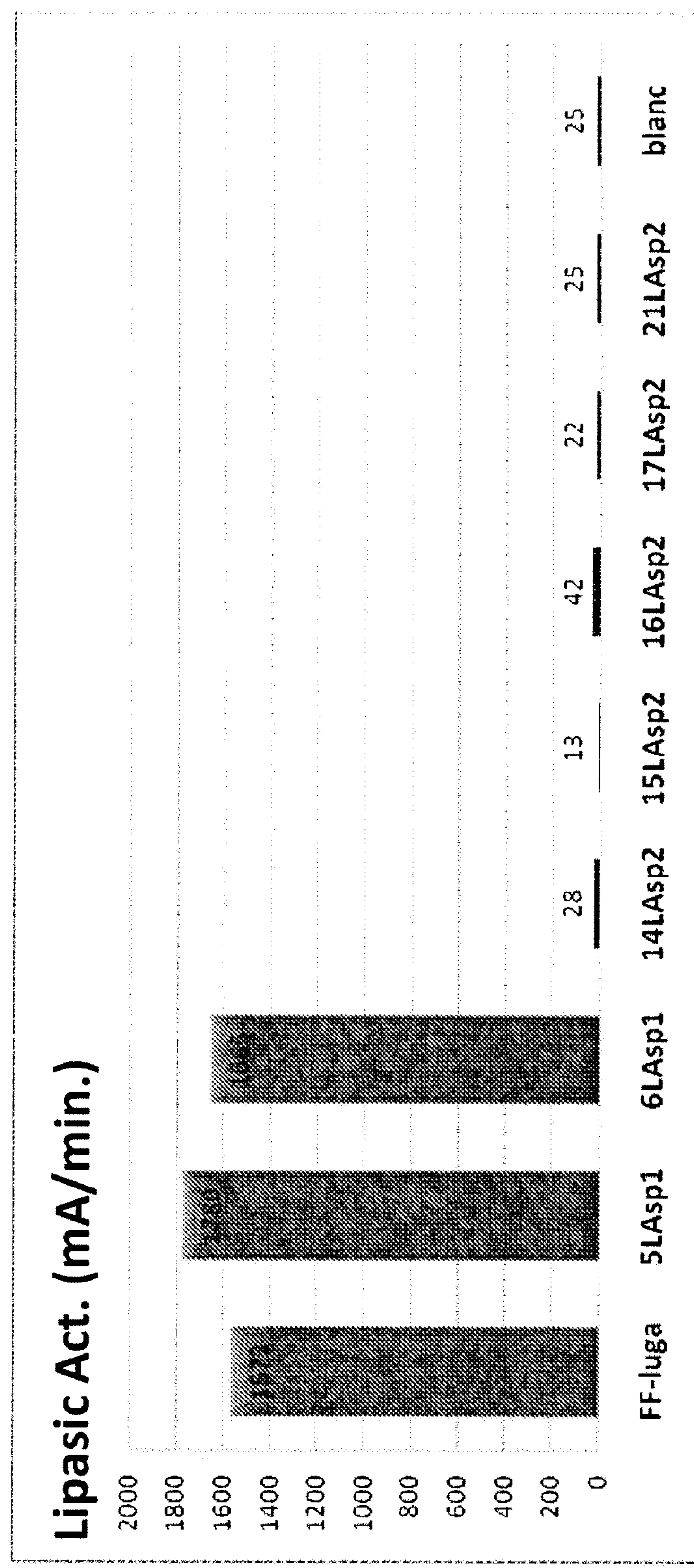

FIG. 7: Lip+/Lip− phenotype analysis to verify the insertion at the LIP2 locus. The transformants obtained with the targeted integration cassette at the LIP2 locus are cultivated in an oleic acid rich medium (YPD2O2). The lipase activity in the supernatant of the strains containing different copies of the asparaginase. The receiver strain Lip+ FF-luga is used as control. Strains with 1 copy at the ADE2 locus (ade2::GUT2-Asp):5LAsp1 and 6LAsp1; strains with 1 copy at the ADE2 locus (ade2::GUT2-Asp):5 LAsp1 and 6LAsp1; strains with 1 copy at the ADE2 locus and 1 copy at the LIP2 locus (ade2::GUT2-Asp, lip2::URA3-Asp): 14LAsp2, 15LAsp2, 16LAsp2, 17LAsp2 and 21LAsp2.

Figure 8:
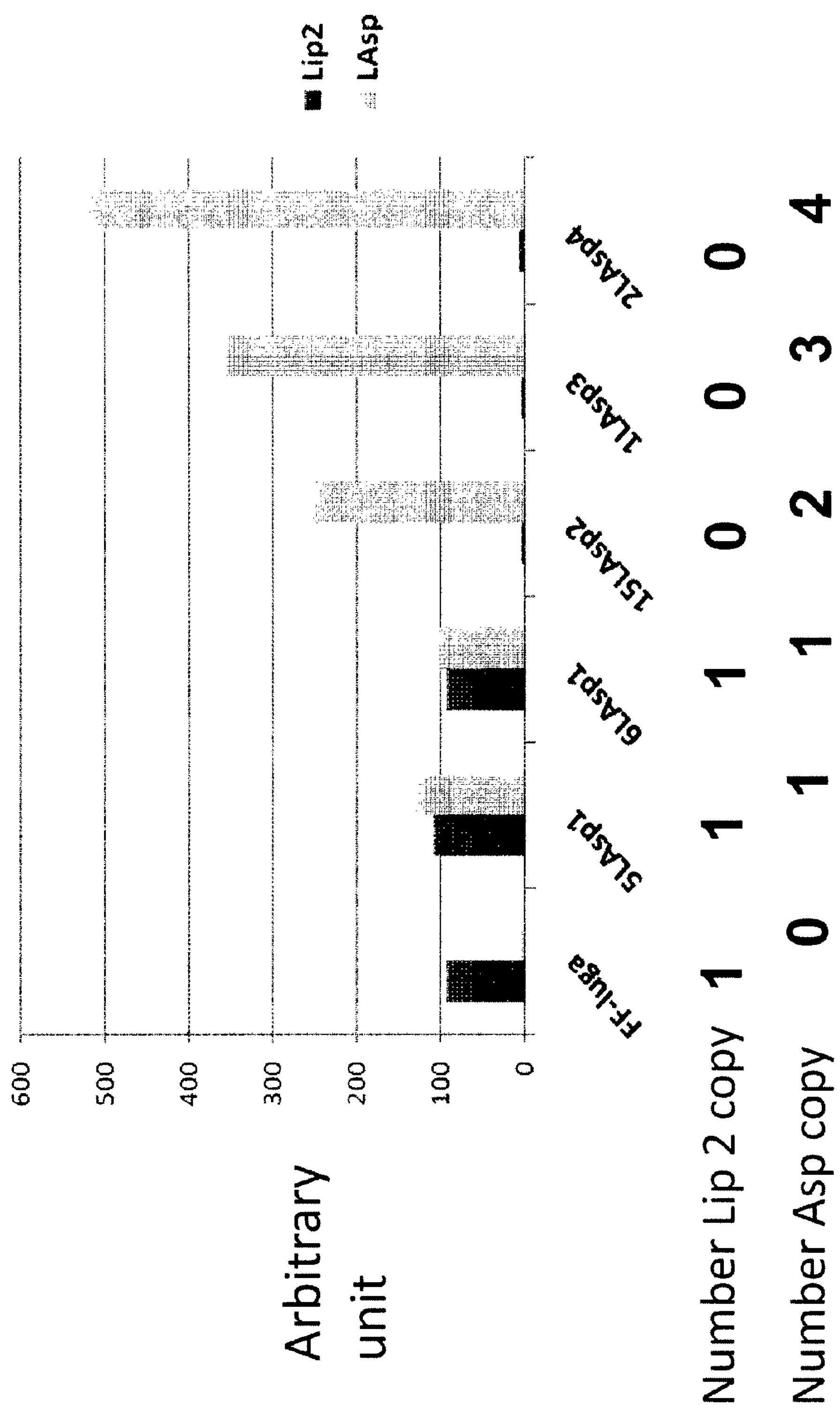

FIG. 8: Determination of the number of copies of the LIP2 gene and Asp via RT-qPCR in the transformants.

EXAMPLES

Example 1

Strains Used in the Examples

The strains used in the method according to the invention are derived from a wild-type strain of *Yarrowia lipolytica*, in particular the wild-type strain *Yarrowia lipolytica* W29 (atcc 20460, indexed under CLIB89 in the Collection of the CIRM (Centre International de Ressources Microbiennes).

Thus, we can use new mutant strains derived from the *Yarrowia lipolytica* strain ATCC 20460 through the intermediary of the strain Po1d [auxotrophic strain got leucine (Leu−) and uracil (Ura−)], described in the publication of G. Barth et al.: *Yarrowia lipolytica*. in Nonconventional Yeasts in Biotechnology: A Handbook (Wolf, K., Ed.), Vol. 1, 1996, pp. 313-388. Springer-Verlag. It is indexed under CLBI139 in the CIRM.

Obtaining these new receiver strains (FF-lu, FF-lug (CNCM I-3911), FF-lua (CNCM I-3912), FF-luga (CNCM I-3913)) will be described later.

Obtaining the Strains

The mutant receiver strains usable in the method according to the invention can be obtained from the Po1d strain, which is derived from the wild-type strain *Yarrowia lipolytica* W29. The Po1d is an auxotrophic strain for leucine (leu−) and uracil (ura−). It is described in the publication of G. Barth et al.: *Yarrowia lipolytica* in: Nonconventional Yeasts in Biotechnology: A Handbook (Wolf, K., Ed.) Vol. 1, 1996, pp. 313-388. Springer-Verlag, Berlin, Heidelberg, N.Y. It is listed as CLIB139 in the CIRM collection. Mutant strains usable in the method according to the invention can be obtained by the insertion of the gene deletion, thereby conferring auxotrophy or a growth defect in certain media, in which the gene has a deletion, if possible a deletion that cannot be reversed, which advantageously corresponds to a complete deletion of the gene. The corresponding gene can be used as selection markers for the selection of transformants having integrated the integration cassettes. The deletions will have a significant deletion compared to the corresponding cassette used for the construction of the selection markers in order to reduce the conversion rate.

1. Deletion of the GUT2 gene (Δgut2-744), construction of the GUT2 marker and obtaining the mutant strain FF-lug (CNCM I-3911).

1.1 Deletion of the GUT2 gene (Δgut2-744)

To obtain this strain, the procedure is as follows:

1) selection of the gene of interest that is to be deleted;

2) construction of a disruption cassette by cloning or by PCR ("Polymerase Chain Reaction") by amplifying the upstream region of the gene ("promoter" region, symbolized by P) and the downstream region of the gene (terminator" region symbolized by T);
3) introduction of a selection marker containing on either side a recombination sequence (advantageously a loxP or loxR sequence or derivative) allowing a recombination between it for the elimination of the marker (advantageously a loxP type sequence that allows recombination under the action of the cre recombinase);
4) transformation with the disruption cassette and selection of the strains with the gene of interest deleted (transformation and selection of the transformants) and verification of the disruption of the gene;
5) transformation with a vector allowing the expression of the recombinase (advantageously the cre recombinase, which allows the recombination of the loxP/loxR sequences and elimination of the marker);
6) isolation of a clone having the deletion of the gene of interest and having lost the recombinase expression plasmid.

Using the auxotrophic mutant FF-lu (Leu−, Ura−), we constructed a mutant *Y. lipolytica* FF-lug auxotrophic for leucine and uracil (Leu−, Ura−) and incapable of using glycerol as carbon source (gly−). The first step is the construction of the FF-lug::URA3 strain prototrophic for uracil (Leu−, Ura+) through deletion of the GUT2 gene via the gut2::URA3ex disruption cassette by transforming the PCR GUT2-PUexT (JME744) fragment and selecting the Ura+ on YNBcasa. We select the auxotrophs for uracil (Leu+, Ura−) by excision of the URA3ex marker by transforming with the replicative vector pRRQ2 containing the Cre recombinase and the LEU2 marker (Cre-LEU2) and by selecting the auxotrophic transformants for uracil, Leu+. The loss of the pRRQ2 plasmid is achieved by cultivation on YPD rich medium and by isolation of a clone (Leu−, Ura−, Gly−).

The schematic representation of the construction of these mutants is summarized in Table I below.

TABLE 1

Transformation steps required for the production of the FF-lug mutant

| | Transformation operations | | |
|---|---|---|---|
| Step | Mutant to be transformed | Transformation cassette | Transformed mutant |
| 1 | FF-lu, PO1d, Leu−, Ura− | Gut2-PUexT | JMY1202, Leu−, Ura+, Gly− gut2-PUexT |
| 2 | JMY1202, Leu−, Ura+, Gly−, Gut2-PUexT | pRRQ2 vector (pKS Cre ARS68 LEU2) | JMY1202, Leu−, Ura+, Gly− gut2-PUexT |

The disruption cassette for the GUT2 gene was constructed by amplification of the upstream region (P region; Yali0B: 1873518 . . . 1872400, reverse direction, 1119 bp) and the downstream T region; Yali0B:1870468 . . . 1869652 complementary, 817 bp), which allows the deletion of the ORF of the GUT2 gene (YaliOB1870469 . . . 1872401) and leaves a homology with the selection marker GUT2ex-0.5 (485 bp with the P region and 56 bp in the T region) in order to minimize gene conversions. The ex selection markers are presented in Table 11.

The P and T regions were amplified with the primers G3PD-P1, G3PD-P2, G3PD-T1 and G3PD-T2 (Table 9).

The primers G3PD-P2 and G3PD-T1 contain the rare site I-SceI for the insertion of the excisable URA3ex selection marker. The PT fragment was cloned in pGEM-T (Invitrogen) to produce the pGEM-GUT2-PT (JME743) plasmid. The pGEM-GUT2-PUexT (JME744) disruption plasmid was obtained by insertion of the URA3ex marker at the I-SceI site coming from the JME507 plasmid.

The disruption cassette (3245 pb) was obtained by PCR with the primers G3PD-P1 and G3PD-T2. The PCR product was purified on agarose gel using the Qiagen gel extraction kit. The strains were transformed using the lithium acetate method. The Ura+ transformants were selected on YNBcasa medium.

The Ura+ transformants are obtained with a typical transformation rate (Fickers, 2003). Disruption of the GUT2 gene was verified by PCR with the 5' primers of the P region (G3PDver1) and the 3' primes of the T region (G3PDver2). The JMY1202 gut2::URA3ex mutant was then transformed by the replicative plasmid pRRQ2 (pKS Cre ARS68 LEU 2; JME461). The transformants obtained are screened for excision of the URA3 marker and loss of the cre recombinase replicative expression plasmid achieved by cultivation on YPD rich medium and by isolation of a clone (Leu−, Ura−, Gly−). The JMY1346 mutant (FF-lug) was selected. The sequence of the gut2-844 locus of the JMY1346 mutant was amplified with the primers G3PDver1 and G3PDver2. The PCR product (size 2415 pb) was sequenced. The obtained sequence shows the absence of the Ura3 marker sequence. After excision, the following sequences remain on the genome between P and T of the GUT2 locus:

```
TGCAGCTTTCGAGAACCGACGCCTGGGACCTGTGTCTGTAGGGATAA

CAGGGTAATTCGCTTCGGATAACTCCTGCTATAACGAAGTTATGTAG

GGATAACAGGGTAAT
(SEQ ID NO: 11; or site I-SceI-sequence LoxR-
site I-SceI).
```

1.2 Construction of the GUT2ex marker

For the construction of the GUT2ex marker, the genome sequence of the GUT2 locus was amplified with the primers G3PTS and G3PTR (Table 8) and cloned in the pKs-LPR vector (Fickers et al., 2003, Journal of Microbiological Methods, vol. 55, p: 727-737) at the EcoRI site. It contains 492 bp of promoter, the ORF of the GUT2 gene, (ORF Yali0B: 1870546 . . . 1872384) and 132 bp of the terminator and corresponds to the sequence Yali0B:1872876 . . . 1870417. This ORF contains 2 BamHI sites and 1 EcoRI site that were eliminated by mutagenesis directed by introducing silent mutations. We used the following primers: G3PB1S and G3PB1R for the first BamHI site (ggAtcc in ggCtcc), G3PB2S and G3PB2R for the second BamHI site (ggatcC into ggatcT) and G3PE1S and G3PE1R for the EcoRI site (gaAttc into gaGttc) (Table 9).

The marker may be inserted in both directions. For this GUT2ex0.5 marker, only direction 1 was obtained in the pKS-LPR. After verification by sequencing, the plasmid containing the modified GUT2ex0.5 marker is JME792.

Two other markers GUT2ex 1.0 and GUT2ex 1.5 containing 1 kb and 1.5 kb of promoter respectively were constructed as a result of the difficulty in obtaining transformants using the GUT2ex0.5 marker (paragraph 1.3). These promoters were amplified using DNAg (E150 *Yarrowia lipolytica* strain) with the primers P1KB and PNHE1 and P15KB and PNHE1, respectively. Cloning was done by 3-way ligation between the pKS-LPR (dephosphorylated EcoRI), the PCR product (EcoRI and NheI) and the rest of the modified GUT2ex marker resulting from JME792 (NheI and EcoRI). The GUT2ex 1.0 marker in direction 1 corresponds to JME919 and in direction 2 corresponds to JME920. The GUT2ex1.5 marker in direction 1 corresponds to JME921 and in direction 2 corresponds to JME922.

1.3 Transformation with the GUT2ex0.5, GUT2×1.0 and GUT2ex1.5 markers.

To validate the use of the GUT2ex marker, the GUT2ex0.5 marker was isolated from the JME792 plasmid (pKS-LPR-GUT2ex0.5) by I-SceI digestion and inserted at the I -SceI site of the JMP62 I-SceI (JME801) plasmid to produce the plasmid JMP62Gut2-ex0.5 (JME805).

The JME805 plasmid was digested by NotI and used to transform the FF-lug strain using the lithium acetate method. The transformants were selected on YNBcasa (1% Glycerol) medium supplemented with uracil (100 mg/L). After several attempts, this marker did not make it possible to obtain transformants.

Initially, we hypothesized that the promoter part (492 pb) was too defective. We therefore constructed 2 other markers containing longer promoter parts (cf. paragraph 1.2), i.e., the GUT2x1.0 and GUT2ex1.5 markers. The same results were obtained.

A repression of the use of glucose in the presence of glycerol has been described in *Saccharomyces cerevisiae* yeast for Δgut2 strains. In fact, the FF-lug strain is incapable of growing in the presence of the 2 carbon sources cited earlier. By modifying our transformation method, we obtained transformants. This new transformation method remains identical to the lithium acetate method and to the polyethylene glycol method (Gaillardin et al. 1985) to which an expression phase is added before spreading the transformation on the selective media. This expression phase is carried out as follows: following thermal shock at 42° C. for 10 minutes. The product of the transformation is centrifuged at 2000 rpm for 3 minutes and the cells are washed with 2 mL of TE buffer pH8. This washing is repeated twice. The cells are then taken up with the nutritive medium 1% Yeast Extract 1% Peptones and 0.2% dextrose. They are incubated for 16 hours at 28 degrees, without stirring. Once again, the product is centrifuged at 2000 rpm for 3 minutes and the cells are washed with 2 mL of TE buffer pH8. This washing is repeated twice. The cells are then taken up with 2 mL of TE and are spread over selective media containing 1% glycerol as sole carbon source.

The results of the transformation of the GUT2ex1.0 marker in the FF-lug strain are presented in table 2 below:

TABLE 2

Transformation effectiveness depending on the transformation method

| Type of | Standard method without expression phase | | New method with expression phase | |
|---|---|---|---|---|
| Integration | random | targeted | random | targeted |
| Number of transformants | 0 | 14 | 133 | 615 |
| Transformation rate per μg of DNA | 0 | 187 | 266 | 8215 |
| % of integration | ND | 75% | ND | 100% |

2. Deletion of the ADE2 (Δade2-844) gene, construction of the ADE2 marker and obtaining mutant FF-lua (CNCM I-3912) and FF-lug (CNCM I-3913) strains.

2.1 Deletion of the ADE2 (Δade2-844) gene

To obtain these strains, it is possible to proceed as follows: using the FF-lu mutant, we constructed the FF-lua Leu−, Ura−, Ade− strain and from the FF-lug mutant we constructed the FF-luga Leu−, Ura−, Ade−, Gly− strain.

2.1a Using the auxotrophic FF-lu (Leu−, Ura−) mutant we constructed an FF-lua mutant *Y. lipolytica* strain auxotrophic for leucine, uracil and adenine (Leu−, Ura−, Ade−). The first step is the construction of the FF-lua::URA3 strain prototrophic for uracil (Leu−, Ura+, Ade−) by deletion of the ADE2 gene via the Ade2::URA3ex disruption cassette by transforming the NotI PTAde2-Ura3EX (JME844) cassette and by selecting the Ura+ on YNBcasa, supplemented with adenine (800 mg/L). The uracil auxotrophs (Leu+, Ura−, ade−) are selected by excision of the URA3ex marker by transforming with the replicative vector pRRQ2 containing the Cre recombinase and the LEU2 marker (Cre-LEU2) and by selecting the transformants auxotrophic for uracil, Leu+. The loss of the cre recombinase replicative expression plasmid pRRQ2 is achieved by cultivation on a YPD rich medium and by isolation of a clone (Leu−, Ura−, Ade−). The JMY1409 (FF-lua) mutant was selected.

2.1.b Using the auxotrophic FF-lug mutant (leu−, Ura−) incapable of using glycerol as a carbon source (Gly−), we constructed a mutant FF-luga *Y. lipolytica* strain auxotrophic for leucine, uracil and adenine (Leu−, Ura−, Ade−) and incapable of using glycerol as carbon source (Gly−). The first step is the construction of the FF-luga::URA3 strain auxotrophic for leucine and adenine (Leu−, Ade−, Ura+) by deletion of the ADE2 gene via the ade2::URA3dx disruption cassette by transforming the NotI PTAde2-PUra3ExT (JME844) cassette and by selecting the Ura+ on YNBcasa supplemented with adenine (800 mg/L). We select the uracil auxotrophs (Leu+, Ura−) by excision of the URA3ex marker via transformation with the replicative vector pRRQ2 containing the Cre recombinase and the LEU2 (Cre-LEU2) marker and by selecting the uracil auxotrophic transformants, Leu+. The loss of the pRRQ2 plasmid is achieved by cultivation on YPD rich medium and by isolation of a clone (Leu−, Ura−, Ade−, Gly−). The JMY1404 (FF-luga) mutant was selected.

The schematic representation of the construction of these mutants is summarized in Table 3 below.

TABLE 3

Transformation steps required for the production of the FF-lua and FF-luga mutants

| | Transformation operations | | |
|---|---|---|---|
| Step | Mutant to be transformed | Transformation cassette | Transformed mutant |
| 1 | PO1d, Leu−, Ura− | PTade2-Ura3Ex | JMY1407, Leu−, Ura+ ade2-PUexT |
| 2 | JMY1407, Leu−, Ura+ Ade2-PUexT | pRRQ2 vector, Leu+ selection, Gly− verification, loss of the pRRQ2 plasmid on YPD, isolation of Leu− | JMY1409, Leu−, Ura−, Ade− Ade2-844 FF-lua |
| 1b | JMY1346, Leu−, Ura−, Gly− Gut2-744 | PTade2-Ura3Ex | JMY1396, Leu−, Ura+ Gly− ade2-PUexT |
| 2b | JMY1396, Leu−, Ura+, Gly− Ade2-844 | pRRQ2 vector, Leu+ selection, Gly− verification, loss of the pRRAQ2 vector on YPD, isolation of Leu− | JMY1404, Leu−, Ura−, Ade−, Gly−, Ade2-844 FF-luga |

The disruption cassette for the ADE2 gene (Yali0B23188g; highly similar to tr|Q9P4V1 *Candida boidinii*), which encodes for phosphoribosyl-5-aminoimidazole carboxylase, protein deduced from 565 aa (Yali0B:3030460 . . . 3032157, forward direction) was constructed by amplification of the upstream region (P region; Yali0B:3029011 . . . 3029931, 920 bp) and of the downstream region (T region; 792 pb, Yali0B: 3031871 . . . 3032662) which allows the deletion of the ADE2 gene ORF (Yali0B:3030460 . . . 3032157). The region eliminated is 1939 pb (Yali0B:3029932 . . . 3031870) and only leaves a very weak homology with the ADE2ex selection marker (O by with the P region and 415 bp in the T region) in order to minimize gene conversions. The ADE2ex marker corresponds to the region Yali0B:3029961 . . . 3032280 fragment of 2319 pb. The ex selection markers are presented in Table 11.

The P and T regions were amplified with the following primers: P1ADE2, P2AD2, T12ADE2 and T2AD2 (Table 9).

The primers P2 and T1 contain the rare site I-SceI for insertion of the excisable selection marker URA3ex. Primer T1 also contains the rare site I-CeuI for the insertion of the expression cassette. Primers P1 and T2 contain the rare site NotI for cloning in pHSS6-NotI (JME800). The PT fragment was cloned in the JME800 digested by NotI and dephosphorylated to produce the plasmid pADE2-PT in orientation 1 (direction 1, JME813) or in orientation 2 (direction 2, JME814). The Direction is defined according to the orientation of the site I-SceI: either direction 1 with the I-SceI site directional or direction 2 with the I-SceI site complementary. The disruption plasmid pPTAde2-Ura3Ex (JME844) was obtained by insertion of the URA3ex marker at the I-SceI site of the JME813 plasmid.

The disruption cassette was obtained by NotI digestion and purification of the 3,089 pb band. The Po1d strain was transformed using the lithium acetate method. The Ura+ transformants were selected on YNBcasa medium supplemented with adenine (100 mg/L). The typical concentrations necessary for complementation of an auxotrophy that are used are generally between 100 and 200 mg/L. The Ura+ transformants are obtained with a low transformation rate, around 50 transformants per microgram of DNA, the analysis of the transformants revealed that they contained a conversion of the ura3-302 marker and not the deletion of the ADE2 gene. We performed several disruption assays with increasing concentrations of adenine. To obtain transformation rates of higher than 103 transformants per μg of DNA, it is necessary to have an adenine concentration higher than 400 mg/L in the media. The concentration used for complementation was 800 mg/L. It is only with these conditions that we obtained transformants with a disruption of the ADE2 gene. Contrary to *S. cerevisiae*, the Ade− strains do not show any pink color. On the other hand, the Ade− clones of *Y. lipolytica* have a brown color after several days in a Petri dish and a brown supernatant in liquid medium. Phenotype usable to identify the transformants or the integration of the expression cassette was indeed integrated at the ADE2 locus (sic).

Verification of the sequence of the ade2-844 locus. The sequence of the ade2-844 locus was amplified with the primers ver1ade2 and ver2ade2 (Table 9). The PCR product of size 2204 pb was sequenced. The sequence obtained shows the absence of the URA3 marker sequence. Furthermore, this verification shows the absence of the integration of the 5' and 3' NotI sites of the PUexT disruption cassette. After excision, the following sequences remain on the genome between P and T of the ade2 locus:

(SEQ ID NO.: 12)
TAGGATAACAGGGTAATTATCGCTTCGGATAACTCCTGCTATACGAA

-continued
GTTATGTAGGGATAACAGGGTAATTAACTATAACGGTCCTAAGGTAG

CGA or the following sites I-SceI-LoxR-I-SceI-I-CeuI.

2.2 Construction of the ADE2ex marker

For the construction of the ADE2ex marker, the genome sequence of the ADE2 locus was amplified using the primers ADE2S and ADE2R and cloned in the pKS-LPR vector (Fickers et al., 2003, Journal of Microbiological Methods, vol. 55, p: 727-737) at the site EcoRI. It contains 500 bp of promoter, the ORF of the ADE2 gene (Yali0B23188g) and 125 bp of the terminator and that corresponds to the sequence Yali0B:3029961 . . . 3032280 or 2319 pb. The EcoRI site present in the ORF of the ADE2 gene was eliminated by modifying the gaatTc into gaatCc via mutagenesis directed with the primers ADE2ES and ADE2ER (Table 9). This modified base creates a silent mutation ATT into ATC.

The marker can be inserted in both directions. The ADE2ex marker in direction 1 corresponds to JME798 and in direction 2 to JME799.

2.3 Transformation with the ADE2ex marker

To test the use of the ADE2ex marker, the ADE2ex marker was isolated from the plasmid JME798 (pKS-LPR-ADE2) by I-SceI digestion and inserted at the I-SceI site of the plasmid JMP631-SceI (JME793) to obtain the plasmid JMP62 ADE2ex (JME862). The JME862 plasmid was digested by NotI and used to transform the FF-lua strain using the lithium acetate method. The transformants were selected on YNB-casa medium with uracil (100 mg/L) and adenine. In the bibliography, regarding Ade-mutants of different species of yeasts, selective media are described that are supplemented with adenine at a concentration of 100 to 200 mg/L. In our case for the Ade− mutants mentioned above, the concentration necessary for proper growth of the transformants is 800 mg/L. Under these conditions, we obtain transformation rates similar to the transformation rates obtained with the URA3 marker.

3. Deletion of the LEU2 gene (Δleu2-958 marker), obtaining the FF2-lu, FF-2lug, FF2-lua and FF2-luag mutant strains and construction of the LEU2ΔBamHI marker.

3.1 Deletion of the LEU2 gene (Δleu2-958)

To obtain these strains, we can proceed as follows: using the FF-lu mutant, we constructed the FF2-lu Leu−, Ura− strain. In similar fashion it is possible to construct strains derived from FF-lua, FF-lug and FF-luag having the Δleu2-958 deletion. Using the FF-lug mutant, we can construct the FF2-lug Leu−, Ura−, gly− strain, using the FF-lua mutant we can construct the FF2-lua Leu−, Ura−, ade− strain and using the FF-luag mutant, we can construct the FF2-luang Leu−, Ura−, ade−, gly− strain.

For example, using the FF-lu mutant, we constructed the corresponding *Y. lipolytica* mutant strain having a larger deletion of the LEU2 gene than for the genetic marker leu2-270. The first step is the construction of the FF2-lu::URA3 strain prototrophic for uracil (Leu−, Ura+) by deletion of the leu2-270 gene via the leu2::URA3ex disruption cassette by transforming the NotI cassette resulting from the pPTLeu2-Ura3EX (JME958) plasmid containing this marker and by selecting the Ura+ on YNBcasa. We select uracil auxotrophs (Leu−, Ura−) by excision of the URA3ex marker transforming with the replicative vector pRRQ2 containing the Cre recombinase and the LEU2 marker (Cre-LEU2) and by selecting the uracil auxotrophic transformants, Leu+. The loss of the pRRQ2 plasmid is achieved by cultivation on YPD rich medium and by isolation of a clone (Leu−, Ura−). The same method may be used to obtain the FF2-lua, FF2-lug and FF2-luga mutants.

The schematic representation of the construction of the FF2-lu mutant is summarized in Table 4 below.

TABLE 4

Transformation steps required for the production of the FF2-lu mutant

| | Transformation operations | | |
|---|---|---|---|
| Step | Mutant to be transformed | Transformation cassette | Transformed mutant |
| a1 | FF-lu, Leu−, Ura− JMY195, Po1d | PTLeu2-Ura3Ex | FF-IU+, leu−, Ura+ Leu2-PUexT |
| a2 | FF-IU+, Leu−, Ura+, leu2-URA3 | pRRQ2 vector, Leu+ selection, Ura− verification, loss of the pRRQ2 plasmid on YPD, isolation of Leu− | JMY1516, Leu−, Ura−, leu2-958 FF2-lu |

The disruption cassette for the LEU2 gene was constructed by amplification of the upstream region (P region; Yali0C44989 . . . Yali0C46081, 1092 pb) and of the downstream region (T region; Yali0C47036 . . . Yali0C47932, 897 pb), which allows the deletion of the ORF of the LEU2 gene (Yali0C46082 . . . Yali0C47035, 954 pb) and that leaves only a very weak homology with the LEU2ex selection marker (O bp with the P region and 207 bp in the T region) in order to minimize gene conversions. The Leu2Ex selection marker was strongly homologous with the genetic marker leu2-270 (401 bp with the P region and 710 bp in the T region) because this marker corresponds to a simple StuI deletion of 681 bp of the LEU2 gene. The ex selection markers are presented in Table 11.

The P and T regions were amplified with the primers P1Leu2, P2Leu2, T1Leu2 and T2Leu2 (Table 9).

The P2 and T1 primers contain the rare site I-SceI for the insertion of the Ura3ex excisable selection marker. The T1 primer also contains the rare site I-CeuI for the insertion of the expression cassette. The primers P1 and T2 contain the rare site NotI for cloning in pHSS6-NotI (JME800). The PT fragment was cloned in the JME800 digested by NotI and dephosphorylated to produce the pLeu2-PT plasmid in orientation 1 (direction 1, JME811) or in orientation 2 (direction 2, JME812). The Direction is defined according to the orientation of the I-SceI site: either direction 1 with the I-ScI site in the forward orientation or direction 2 with the I-SceI site in the reverse orientation. The pPTLeu2-Ura3Ex (JME958) disruption plasmid was obtained by insertion of the Ura3ex marker at the I-SceI site of the JME811 plasmid.

The disruption cassette was obtained by NotI digestion and purification of the 3351 pb band. The strains were transformed using the lithium acetate method. The Ura+ transformants were selected on YNBcasa medium.

3.2 Construction of the LEU2n (LEU2exΔBamHI) marker

For the construction of the expression cassettes and of the integration cassettes, the selection markers must not contain the unique sites used for cloning the genes of interest (BamHI, HindIII, KpnI and AvrII). For the construction of the LEU2n (LEU2exΔBamHI) marker, the Leu2-L1 and Leu2-L2 primers were used to create a linker providing the modification ggaatT into ggaatC and possessing the ApaI site (Table 9). The pKS-LPR-Leu2 (JME509) plasmid was digested on the one hand by ApaI and ScaI and, on the other, by BamHI and ScaI. The ApaI-ScaI band of 1471 pb and BamHI-ScaI band of 3300 pb were purified on agarose gel. A 3-way ligation was performed with these 2 bands plus the Leu2L1/Leu2L2 linker. We obtained a plasmid containing the new modified LEU2n marker LEU2exΔBamHI (JME790).

4. Development of the random monocopy integration system with different excisable markers.

The construction was done using different existing excisable markers and markers obtained in this invention (Table 11).

First, we constructed the 2 base vectors named I-SceI or JMP61 I-SceI and JMP62 I-SceuI. Using the JMP61 leu2Ex and JMP62 leu2Ex vectors containing the excisable LEU2 marker, we performed PCT for the entire plasmid with a primer couple: 62claS and 62claR (Table 9). We used the Stratagene "QuikChange® Site-Directed Mutagenesis Kit," which makes it possible to perform directed mutations. The principle, based on PCR amplification, uses primers constructed specifically to force the mutation of the PCR product. Usually used for short insertions/deletions or specific mutations, we used this principle in order to eliminate the Leu2Ex marker by recircularization of the plasmid at the I-SceI site. These 2 primers were also constructed to eliminate the BamHI and AvrII sites contained in the JMP61 Leu2Ex plasmid upstream of the I-SceI site and to restore the ClaI site in order to allow the exchange of the promoter by this unique site. The PCR product obtained is then digested by the restriction enzyme DpnI, which makes it possible to eliminate the parental strand. This parental strand, coming from a strain of *E. coli* dam+ is methylated and, contrary to the newly formed strand, it will be recognized and digested specifically by the DpnI enzyme. After transformation and screening, we obtained the vectors JMP61 I-SceI and JMP62 I-SceI (Table 12).

The other constructions (Table 12) were accomplished using these 2 plasmids. The ligations were performed with the plasmids digested by I-SceI and dephosphorylated and the purified I-SceI purified of the different excisable markers using the corresponding pKS-LPR plasmids (Table 11). For the excisable marker Leu2, we used the plasmid JME790 containing the marker LEU2n (Leu2ΔBamHI).

TABLE 5

Strains obtained:

| Strain | Collection No. | Genotype |
|---|---|---|
| FF-lu | JMY195, Po1d | xpr2-322, leu2-270, ura3-302 |
| FF2-lu | | xpr2-322, leu2-958, ura3-302 |
| | JMY1202 | xpr2-322, leu2-270, ura3-302, gut2-PUext |
| FF-lug | JMY1346 | xpr2-322, leu2-270, ura3-302, gut2-744 |
| | JMY1407 | xpr2-322, leu2-270, ura3-302, ade2-PUexT |
| FF-lua | JMY1409 | xpr2-322, leu2-270, ura3-302, ade2-844 |
| | JMY1396 | xpr2-322, leu2-270, ura3-302, gut2-744, ade2-PUexT |
| FF-luga | JMY1404 | xpr2-322, leu2-270, ura3-302, ade2-744, ade2-844 |
| 5LAsp1 | 1 copy | ade2 ::GUT2-Asp |
| 6LAsp1 | 1 copy | ade2 ::GUT2-Asp |
| 14LAsp2 | 2 copies | ade2 ::GUT2-Asp lip2 ::URA3-Asp |
| 15LAsp2 | 2 copies | ade2 ::GUT2-Asp lip ::URA3-Asp |
| 16LAsp2 | 2 copies | ade2 ::GUT2-Asp lip2 ::URA3-Asp |
| 17LAsp2 | 2 copies | ade2 ::GUT2-Asp lip ::URA3-Asp |
| 21LAsp2 | 2 copies | ade2 ::GUT2-Asp lip ::URA3-Asp |
| 1LAsp3 | 3copies | ade2 :: GUT2-Asp lip2 ::URA3-Asp leu2 ::ADE2-Asp |
| 2LAsp4 | 4 copies | ade2 :: GUT2-Asp lip2 ::URA3-Asp leu2 ::ADE2-Asp ura3 ::LEU2-Asp |

5. Construction of the base, cloning and expression vectors.

5.1 Base and cloning vectors.

The base vector was constructed using the JMP62 vector by retaining only the *E. coli* shuttle portion coming from the pHSS6 plasmid. After digestion of the JMP62 vector by NotI, the 2210 pb band containing the origin of replication for *E. coli* and the resistance to Kanamycin was isolated and purified then religated to thus form the base vector named pHSS6-NotI (JME800). Using this base vector, we constructed the cloning vector (FIG. 2) through the ligation of 2 linkers and a PCR fragment containing the terminal sequences of the LIP2 lipase of *Y. lipolytica* contained in the JMP62 vector. The linkers were made via couple synthesis of the 5' phosphorylated primer, i.e., the linker 1 with the primers link 1 and link 11 and the linker 2 with the primers link 2 and link 22 (Table 10). These linkers create a cloning multisite containing respectively the sites ClaI and BamHI for the insertion of a promoter and the sites BamHI/HindIII and SacII/KpnI/AvrII for the insertion of the gene of interest. We also introduced a "consensus" sequence in −4 and −1 of the ATG: $C^{-4}$ A C $A^{-1}$. This sequence is present for the *Y. lipolytica* genes that encode for strongly expressed proteins. Thus, for an expression with this sequence, the cloning of the gene of interest is done by HindIII and without this sequence by BamHI in the 5' position. The PCR fragment (840 pb) containing the terminal sequences of LIP2 was obtained with the primers PDX2Xho and Lip2Thc. This fragment was digested by AvrII and NotI to obtain the 179 pb fragment containing only the terminal sequences of LIP2. We added a unique HindIII site in order to allow the exchange of these terminal sequences by AvrII and HindIII. We introduced 2 rare sites of the restriction enzyme I-CeuI on either side of the multisite and the terminal sequences. This I-CeuI double site makes it possible to isolate and purify the expression cassette for cloning in integration vectors.

A 3-way ligation was performed with the 2 linkers, the 179 pbAvrII/NotI band pb and the dephosphorylated base vector pHXX6 NotI to obtain the cloning vector named pVC (JME829).

5.2 Expression vector

The expression vector was constructed using the pVC cloning vector digested by ClaI and BamHI. The reduced promoter pPOX2 (1017 pb) was isolated and purified after digestion by ClaI and BamHI of the JMP62 vector (Table 12). A ligation of the pVC and the pPOX2 promoter was carried out to obtain the expression vector named pVC-pPOX2 (JME830), Table 6.

TABLE 6

Vectors used to construct the expression vector

| Description | Vector name | Collection No. |
|---|---|---|
| Base vector | pHSS6-NotI | JME800 |
| Cloning vector | pVC | JME829 |
| Expression vector | pVC-pPOX2 | JME830 |

6. Selection of the insertion loci and construction principle for the integration vectors. We chose the following different loci:

6.1 Leu2-270 locus

This locus has often been used as homologous integration target via simple "crossing over" (eg. Bordes et al., 2007), but with this genome marker we obtain a high conversion rate (it corresponds to a small StuI deletion of 681 pb that leaves a 5' region of 401 pb (Yali0C:46411 . . . 46537) and a 3' region of 710 pb (Yali0C:46528 . . . 46948) that allows a double recombination with the LEU2 selection marker used in our vectors. Thus, a high conversion rate is generally observed during transformations of expression cassettes containing this marker. To reduce the conversion rate, as a first step, we chose to insert an expression cassette at the leu2-270 locus in order to eliminate these homology regions in 5' and 3' regions. Thus, during an insertion of a new expression cassette containing the LEU2 marker at another locus, the conversion rate is sharply reduced. Alternatively, it is possible to construct a strain with the marker leu2-958 as described in chapter 3.

6.2 Ura3-320 locus

The deletion was performed via double crossing-over leaving only 21 pb in 5' position (Yali0E:3171873 . . . 3171893) and 108 pb in 3' position (Yali0E:3175134 . . . 3175241). The deleted fragment (695 pb) was replaced with the following expression cassette: promoter of the XPR2 gene and the SUC2 gene encoding for the invertase of *Saccharomyces cerevisiae* in the reverse direction (3240 pb, Yali0E: 3171894 . . . 3175133). Integration in this Ura3-320 makes it possible to eliminate the SUC2 gene coming from *S. cerevisiae* in the production strain and to simply and quickly screen the Suc− transformants (absence of any growth on medium containing only saccharose as sole carbon source) as described in FIG. 6.

6.2 Lip2 locus

The LIP2 gene encodes for the Lip2p lipase of *Y. lipolytica*. Its expression is induced in the presence of fatty acids and triglycerides (Pignede et al., 2000). In this invention, the expression of the proteins of interest is placed under the strong and inducible promoter pPOX2. This promoter is also inducible by fatty acids like oleic acid. Integration at the LIP2 locus makes it possible to invalidate the LIP2 gene and to obtain the absence of expression of the Lip2P lipase in the culture supernatants at the time of production. Furthermore, this makes it possible to simply and quickly screen the Lip2− transformants (absence of any degradation of a tributyrin emulsion visible on gelosed medium or absence of any lipase activity in the culture supernatant as described in FIG. 7).

6.4 Ade2 locus

In this invention, new Ade− strains were constructed, as well as the Ade2ex selection marker. For the disruption of the ADE2 gene the P and T sequences were amplified. These same sequences were thus used in the integration vectors. Thus, no additional construction was necessary for this locus. If the receiver strain used is FF-lug, insertion at the ADE2 locus renders the Ade− strain, which creates a new auxotrophy, which may be used to introduce an additional copy of the gene of interest. This disruption is also associated with a quickly identifiable phenotype (brown coloration of the disrupted colonies on rich medium in a Petri dish, brown coloration of the culture medium).

This list or these Locus/Marker combinations is not exhaustive. All other combinations are possible, preferably with a locus whose disruption creates a rapidly visualizable phenotype that allows rapid screening of the transformants having correctly integrated the expression cassette at the locus. Other loci and other markers can be chosen or other combinations can be produced.

6.5 Construction principle for the integration vectors. The construction principle for the integration vectors is described in FIG. 3. The different integration cassettes at defined loci were constructed using an identical methodology. Using the DNAg of the E150 strain, we amplified the promoter part named P and the terminator part named T of the gene to be disrupted. The P and T fragments must preferably have a size between 800 and 1000 pb to achieve effective homologous double recombination in *Y. lipolytica*. The primers used are named P1/P2 for the P fragment and T1/T2 for the T fragment followed by the name of the locus (Table 9). The primers P1 and P2 contain a rare site 1, here the NotI site, to allow cloning in the base vector pHSS6-NotI and also to release the expression cassette. The primers P2 and T1 contain two other rare sites, rare site 2 and rare site 3, here the sites I-SceI and I-CeuI, respectively, which allow the fusion via PCR of the 2 fragments and the subsequent cloning of the selection marker at rare site 2, here the site I-SceI, and of the expression cassette at rare site 3, here the site I-CeuI. PCR fusion is therefore achieved using a purified mixture of the 2 P and T fragments and of the P1/T2 primer couple. The PT fragment obtained is digested by NotI and is then cloned by ligation in the vector pHSS6 digested by NotI and dephosphorylated. The integration vectors are named pPT followed by the name of the locus (Table 7).

Description of the P and T fragments of the different loci:

Leu2-270 locus: The regions amplified for homologous double recombination are 1092 pb for the P region (Yali0C: 44989 . . . 46081) and 897 pb for the T region (Yali0C: 47036 . . . 47932). The region that will be eliminated is 954 pb (Yali0C:46082 . . . 47035). This region eliminates the entire 5' region of the marker Leu2 (401 pb) and a portion of the 3' region (503 pb). A homology of 207 pb of the 3' region of the Leu2 marker remains.

Ura3-302 locus: The regions amplified for the homologous double recombination are 1197 pb for the P region (Yali0E: 3170698 . . . 3171894) and 1013 pb for the T region (Yali0E:3175412 . . . 3176424). The region that will be eliminated is 3516 pb (Yali0E:3171895 . . . 3175411). This region eliminates the entire expression cassette pXPR2+SUC2 and the 3' region of the Ura3 marker (280 pb). A homology of 200 pb of the 5' region of the Ura3 marker remains.

Lip2 locus: The regions amplified for homologous double recombination are 1123 pb for the P region (Yali0A: 2185897 . . . 2187019) and 961 pb for the T region (Yali0A: 2187883 . . . 2188843). The region that will be eliminated is 863 pb (Yali0C:2187020 . . . 2187882). This region eliminates almost all of the LIP2 gene. A homology of the 3' region of 148 pb of the LIP2 gene remains. Ade2 Locus: The regions amplified for homologous double recombination are 920 pb for the P region (Yali0B:3029011 . . . 3029931) and 792 pb for the T region (Yali0B:3031871 . . . 3032662). The region that will be eliminated is 1939 pb (Yali0B:3029932 . . . 3031870), which leaves only a very weak homology with the selection marker ADE2ex (O bp with the P region and 415 bp in the T region) in order to minimize gene conversions.

For each locus, the P and T regions were amplified using the primer couple named P1/P2 and T1/T2 followed by the name of the locus (Table 9). Then the PT fusion was performed with the P1/T2 couple.

Using these pPT vectors, different excisable markers were introduced by cloning at the I-SceI site. This site allows oriented cloning of the marker. We chose to orient the marker in the reverse direction of the expression cassette. The integration vectors obtained are named pPT followed by the name of the locus followed by the name of the excisable marker inserted (Table 7).

The Locus/Marker combinations are given only as examples; different combinations are possible.

TABLE 7 list of integration vectors

| Locus | Vector name | I-Scel orientation | Collection No. | Marker | Vector name | Collection No. |
|---|---|---|---|---|---|---|
| LIP2 | pPTLip2 | | | URA3ex | pPTLip2-Ura3ex | JME815 |
| | | Direction 1 | JME806 | GUT2-0.5ex | pPTLip2-Gut2-0.5ex | JME816 |
| | | Direction 2 | JME807 | | | |
| URA3 | pPTUra3 | Direction 1 | JME809 | LEU2nex | pPTUra3-Leu2nex | JME817 |
| | | Direction 2 | JME810 | | | |
| LEU2 | pPTLeu2 | Direction 1 | JME811 | ADE2ex | pPTLeu2-Ade2ex | JME818 |
| | | | | URA3ex | pPTLeu2-Ura3ex | JME958 |
| | | Direction 2 | JME812 | | | |
| ADE2 | pPTAde2 | | | GUT2-0.5ex | pPTAde2-Gut2-0.5ex | JME819 |
| | | Direction 1 | JME813 | URA3ex | pPTAde2-Ura3ex | JME844 |
| | | Direction 2 | JME814 | | | |

7. Construction principle for integration vectors for the expression of a protein of interest. Cloning of a gene of interest is achieved in only 2 cloning steps. The first step is a subcloning in the pVC expression vector to obtain the pVC-gene of interest vector under the control of the PDX2 promoter (other strong promoters may be used such as the promoter hp4d or inducible promoters). This pVC-gene of interest vector is digested by I-CeuI to isolate and purify the expression cassette. The second step is the cloning of this I-CeuI expression cassette in the integration vectors. The integration cassette/expression cassette vector is isolated and purified after digestion by NotI before transformation in *Y. lipolytica* (FIG. 3).

Example 2

Construction and Use of an Integration/Expression Cassette for the Targeted Insertion of a Gene Encoding for a Therapeutic Protein of Interest not Produced by *Y. lipolytica*

We took as example the L-asparaginase protein of *Erwinia chyrsanthemi*. The gene encoding for this protein was introduced into the vector pVC-pPOX2 at the HindIII/AvrII site. To do this, a fusion PCR was performed between the prepro-LIP2 sequence and the portion of the sequence of the gene encoding for the mature form of the L-asparaginase protein. PCR was performed with the primers preproLip2 and Lip2KR to amplify the pre-pro-LIP2 sequence and with the Laspens and Lasprev primers to amplify the sequence encoding for the mature protein. Then, by mixing the 2 PCR products obtained, the fusion with the preproLIP2 and pLasprev primers was carried out.

The preproLip2 primer contains the HindIII site and the Lasprev primer the AvrII site for cloning the fusion product in the pCV-pPOX2. The vector pVC-pPOX2-preproLip-LAsp (JME898) containing the expression cassette of the L asparaginase protein is thus obtained (Table 8). From this vector, the expression cassette is extracted through digestion by the restriction enzyme I-CeuI and purified. This cassette is then cloned in the different integration vectors at the I -CeuI site. The different integration/expression vectors obtained are described in Table 8.

TABLE 8

Integration/expression vectors obtained:

| Descriptions | Vector name | Collection No. |
|---|---|---|
| Expression vector | pVC-pPOX2-LAsp | JME898 |
| Int. vector Ura3 locus | pPTUra3-Leu2nEx-LAsp | JME923 |
| Int. vector Ade2 locus | pPTAde2-Gut2-0.5Ex-LAsp | JME924 |
| Int. vector Ade2 locus | pPTAde2-Ura3Ex-LAsp | JME925 |
| Int. vector Leu2 locus | pPTLeu2-Ade2Ex-LAsp | JME926 |
| Int. vector Lip2 locus | pPTLip2-Ura3Ex-LAsp | JME927 |
| Int. vector Ade2 locus | pPTAde2-Gut2-1.0Ex(d1)-LAsp | JME941 |
| Int. vector Ade2 locus | pPTAde2-Gut2-1.0Ex(d2)-LAsp | JME942 |
| Int. vector Ade2 locus | pPTAde2-Gut2-1.5Ex(d1)-LAsp | JME943 |
| Int. vector Ade2 locus | pPTAde2-Gut2-1.5Ex(d2)-LAsp | JME944 |

The integration/expression cassettes are obtained by digestion of the restriction enzyme NotI of the different integration/expression vectors. These cassettes are then extracted and purified in order to eliminate the *E. coli* exogenous DNA sequences.

Example 3

Transformation of the Integration/Expression Cassettes of the L-asparaginase Protein in *Y. lipolytica*

It is possible, for example, to introduce successively 4 copies of the expression cassette of L-asparaginase in the 4 loci mentioned earlier in the FF-luga strain.

1 Insertion of the First Copy at the ADE2 Locus.

The first expression cassette was introduced by transformation of the FF-luga strain at the ADE2 locus using the integration/expression cassette PTAde2-Gut2-1.0Ex-LAsp from the vector JME941. The transformants are selected on selective YNBcasa medium supplemented with uracil and adenine and containing 1% glycerol as sole carbon source. The transformants obtained are isolated on this same selective medium and integration at the locus is verified by PCR using the primers Ver1ade2 and Ver2ade2 located upstream and downstream of the integration sequences.

The transformation rate obtained is 8.2 $10^3$ transformants per μg of DNA transformed.

Verification of integration at the Ade2 locus via PCR showed that 100% of the transformants integrated the LAsp expression cassette at this locus.

We retained 2 transformants named 5LAsp1 and 6LAsp1 (Table 5). The first figure at the start of the name give the number of the transformant and the second figure at the end of the name gives the number of copies of the LAsp expression cassette.

2 Insertion of the Second Copy at the LIP2 Locus.

The second expression cassette was introduced by transformation of the transformant 5LAsp1 at the LIP2 locus using the integration/expression cassette PTLip2-Ura3Ex-LAsp resulting from the vector JME927. The transformants were selected on selective YNBcasa medium supplemented with adenine and containing 1% glucose as sole carbon source. The transformants obtained are isolated on this same selective medium and integration at the locus is verified by PCR using the Ver1lip2 and Ver2lip2 primers located upstream and downstream of the integration sequences. The transformation rate obtained is 1.1 $10^4$ transformants per μg of DNA transformed. Verification by PCR of integration at the LIP2 locus showed that 75% of the transformants integrated the LAsp expression cassette at this locus. Alternatively, verification of integration of the expression cassette at the LIP2 locus can be accomplished by measuring the lipase activity as demonstrated in FIG. 7.

We retained 5 transformants named 14LAsp2, 15LAsp2, 16LAsp2, 17LAsp2 and 21LAsp2 (Table 5).

3 Insertion of the Third Copy at the LEU2 Locus.

The third expression cassette was introduced by transformation of the transformant 15LAsp2 at the LEU2 locus using the integration/expression cassette PTLeu2-Ade2Ex-LAsp resulting from the vector JME926. The transformants were selected on selective YNBcasa medium containing 1% glucose as sole carbon source. The transformants obtained are isolated on this same selective medium and integration at the locus is verified by PCR using the Ver1leu2 and Ver21leu2 primers located upstream and downstream of the integration sequences.

The transformation rate obtained is 1.6 $10^4$ transformants per μg of DNA transformed.

Verification by PCR of integration at the LEU2 locus showed that 20% of the transformants integrated the LAsp expression cassette at this locus.

We retained 1 transformant named 1LAsp3 (Table 5).

4 Insertion of the Fourth Copy at the URA3 Locus.

The fourth expression cassette was introduced by transformation of the transformant 1 LAsp3 at the URA3 locus using the integration/expression cassette PTUra3-Leu2nEx-LAsp resulting from the JME923 vector. The transformants were selected on selective YNB medium containing 1% glucose as sole carbon source. The transformants obtained were isolated on this same selective medium and integration at the locus was verified by PCR using the Ver1Ura3 and Ver2Ura3 primers located upstream and downstream of the integration sequences.

The transformation rate obtained is 5.25 $10^3$ transformants per μg of DNA transformed. PCR verification of integration at the URA3 locus showed that 87% of the transformants integrated the LAsp expression cassette at this locus, 87% of the transformants are Ura− (FIG. 6).

We retained 1 transformant named 2LAsp4 (Table 5).

This last strain indeed contains at least one supplemental copy (see FIG. 5 (electrophoresis gel) and FIG. 8 RT-qPRC quantification.

5 Insertion Procedure Variant:

The invention may also be implemented according to the following steps: First, the 4 (for example) transformations are carried out one after the other. Then the insertions are screened using different markers. This explains the interest, if the Cre-lox system is not used, of having as many different screening systems as copies to be integrated.

Example 4

Analysis of the Expression of L-Asparaginase Based on the Number of Copies Integrated The expression of L-Asparaginase was analyzed in production using the different transformants obtained containing 1 to 4 copies. Production was carried out in a 250 mL flask containing 25 mL of rich medium composed of 1% Yeast Extract, 2% Bacto Tryptone, 1% Glucose, 50 mM of sodium phosphate buffer pH16.8 and a 2% oleic acid emulsion (called Y1T2D1O2). The oleic acid serves as inducer of the pPOX2 promoter. The expression is analyzed by gel electrophoresis under denaturing and reducing conditions using the supernatant of the cultures. Gel electrophoresis is revealed by colloidal blue staining and by western blot using polyclonal rabbit antibodies directed against L-Asparaginase. The results of this analysis are presented in FIG. 5.

Example

Dish Screening of the Transformants Obtained by Insertion of the Integration/Expression Cassette at the URA3 Locus As described previously, insertion at the URA3 locus makes it possible to eliminate the heterologous gene SUC2 encoding for invertase from *S. cerevisiae*. The transformants having integrated the expression cassette then become Suc2−. They are no longer able to grow on saccharose as sole carbon source. The transformants are streaked onto 2 rich media: YPD (1% glucose) and YPS (1% saccharose). The results of this analysis are presented in FIG. 6. Through this screening we confirm the results obtained by PCR analysis with the Ver1Ura3 and Ver2Ura3 primers.

Example 6

Screening of the Transformants Obtained by Insertion of the Integration/Expression Cassette at the LIP2 Locus As described previously, insertion at the LIP2 locus makes it possible to eliminate the LIP2 gene encoding for the extracellular lip2p lipase of *Y. lipolytica*. The transformants having integrated the expression cassette then become Lip2−. During production in a medium containing an inducer like oleic acid, the transformants no longer secrete lipase in the culture supernatant. Screening is performed by cultivation in production medium Y1T2D1O2 for 48 hours at 28° C. and stirring at 180 rpm. The presence of lipase in the supernatant is detected by a microplate enzyme assay from 20 μL of supernatant. The results of this analysis are presented in FIG. 7. Through this screening, we confirm the results obtained by PCR analysis with the Ver1Lip2 and Ver2Lip2 primers.

Example 7

Analysis of the Transformants Obtained by RT-qPCR

The number of copies integrated can be analyzed via real time quantitative PCR via specific amplification of an amplicon (150 pb) of the gene encoding for L-Asparaginase. Using the DNAg of the transformants obtained, we performed RT-qPCR using the specific primers LAsp1 and LAsp2 of the gene encoding for L-Asparaginase and the specific primers Act4 and Act5 of the gene encoding for the actin of *Y. lipolytica*. This RT-qPCR was performed using the LightCycler Faststart DNA Master SyBR Green I Kit (Roche). The actin amplicon makes it possible to be a so-called household gene whose expression is known in order not to be modified between the conditions assayed and in our case a gene present in a single copy in the genome. Thus, the results are standardized with this amplicon. We also performed RT-qPCR with the help of specific Lip2-1 and Lip2-2 primers of the gene encoding for the Lip2p lipase of *Y. lipolytica* to verify the absence of the gene as of the second expression cassette integrated at the LIP2 locus. The results of this analysis are presented in FIG. 8.

TABLE 9

Lists of primers used for the disruption cassettes, the verifications and the construction of new markers.

| | Primer | 5'-3' | F/R | Sites |
|---|---|---|---|---|
| Leu2EX | LEU2-L1 | GATCTGCTAGTGTATAAGACTCTATAAAAAGGGCC | F | ΔBamHI |
| | LEU2-L2 | CTTTTTATAGAGTCTTATACACTAGCA | R | ΔBamHI |
| GUT2 marker | PG3PTS | CCGGAATTCCTGACCAGTCTCACATCCGACC | F | EcoRI |
| | PG3PTR | CCGGAATTCTAAAGCAGATACTCAACAACTCAGCAATAGTC | R | EcoRI |
| | G3PB1S | GGAGCTACCGGCTCCGGTATCGC | F | ΔBamHI |
| | G3PH1R | GCGATACCGGAGCCGGTAGCTCC | R | ΔBamHI |
| | G3PB2S | CGGAAACGCTGGATCTTTCAACATCAAGGCC | F | ΔBamHI |
| | G3PB2R | GGCCTTGATGTTGAAAGATCCAGCGTTTCCG | R | ΔBamHI |
| | G3PES | GGAGCAGGAGTTCAACACCGGTGTCG | F | ΔEcoRI |
| | G3PER | CGACACCGGTGTTGAACTCCTGCTCC | R | ΔEcoRI |
| AGUT2 | G3PD-P1 | GCAGATCCACTGTCAAGCCG | F | |
| | G3PD-P2 | GCTAGGGATAAACAGGGTAATGCGGTAGGAAAGAGAAGTTCCGCG | R | I-SceI |
| | G3PD-T1 | GCATTACCCTGTTATCCCTAGCCGGACTATTTCCCCGCAGC | F | I-SceI |
| | G3PD-T2 | GCAGCCAGCAGCACGTAGTAG | R | |
| | G3PD-Ver1 | GAATGACGGGGGCAACGCAG | F | |
| | G3PD-Ver2 | CAGCAGCCACAAATAGCAGACTGCC | R | |
| pGUT2-1.0 and 1.5 | P1KB | CCGGAATTCCGTGACAACGGATGATGCTGTCACATGACG | F | EcoRI |
| | P15KB | CCGGAATTCCTGTTGCCATGCACAGCTCCACTCAACG | F | EcoRI |
| | PNHE1 | TCCCGCTAGCCGAGGTATGCAAGGACGAGTGC | R | NHeI |
| ADE2 locus | P1ADE2 | ATAAGAATGCGGCCGCGCGAGTGAGAGCCGATACCAAGGGATGCGAG | F | NotI |
| | P2ADE2 | CATTACCCTGTTATCCCTACAGACACAGGTCCCAGGCGTCGGTTCTCG | R | I-SceI |
| | T1ADE2 | CTAGGGATAACAGGGTAATTAACTATAACGGTCCTAAGGTAGCGACCTCG GAAACCACTCTGCCAGTCATCGGTGTC | F | I-SceI/ CeuI |
| | T2ADE2 | ATAGTTTAGCGGCCGCGGAAGCGTGT-CAACGACATGTTCCCTCTTCATACC | R | NotI |
| | Ver1Ade2 | CGACGATAGAGCAGGTCTCACTGTTGGGAATGCTG | F | |
| | Ver2Ade2 | CTACACTGACGAAGTGGACATCCCGGCTTGGACTG | R | |

TABLE 9-continued

Lists of primers used for the disruption cassettes, the verifications and the construction of new markers.

| | Primer | 5'-3' | F/R | Sites |
|---|---|---|---|---|
| ADE2 marker | ADE2S | CGCGAATTCGCCTGCTTGAAAGAAGTGAGTGGTATGCTCGG | F | EcoRI |
| | ADE2R | CGCGAATTCCATTGCCACGACCTGTTAAAAGACAAGATGACC | R | EcoRI |
| | ADE2ES | GCTGGCCATCCGAATCCTGGCTGCTTACGACGCC | F | AEcoRI |
| | ADE2ER | GGCGTCGTAAGCAGCCAGGATTCGGATGGCCAGC | R | AEcoRI |
| Lip2 locus | P1Lip2 | ATAAGAATGCGGCCGCGTGGTACGTTTCGTCGCATCGGACGAG | F | NotI |
| | P2Lip2 | CATTACCCTGTTATCCCTAGAGAGCTGGTACTTGGGTATCAATTGAGG | R | I-SceI |
| | T1Lip2 | CTACCGATAACAGGGTAATTAACTATAACGCTCCTAAGGTAGCGACCTGA TCCACCCTCCTCTCTCCAACG | F | I-SceI/ CeuI |
| | T2Lip2 | ATAGTTTAGCGGCCGCGTGGACACAAGGAAGTATGCGGTCGTCGTCG | R | NotI |
| | Lip2Ver1 | CTCTGTCAGTGTTCGGATAAGTCCTTAGATCACC | F | |
| | Lip2Ver2 | CCTCACTTCTGTCACAGATGATGCATTCAACAC | R | |
| Leu2 locus | P1Leu2 | ATAAGAATGCGGCCGCGACACTACTCTGGCTACAGCTTGCGGTACTG | F | NotI |
| | P2Leu2 | CATTACCCTGTTATCCCTAGCTCGAATAACATTCACAGGCTTGGTG | R | I-SceI |
| | T1Leu2 | CTAGGGATAACAGGGTAATTAACTATAACGGTCCTAAGGTAGCGAGGTGT GTTTGTAGTGGAGGACAGTGGTACG | F | I-SceI/ I-CeuI |
| | T2 Leu2 | ATAGTTTAGCGGCCGCGTACTGAACCGACTTTGGTGCTTGCACTC | R | NotI |
| | Leu2Ver1 | CTCCACGCTAATGCCCATCATACTCTGTTTGGC | F | |
| | Leu2Ver2 | CCTGGCGTTACAAAGCCGAGGGAGACAGCCTTGAC | R | |
| Ura3 locus | P1Ura3 | ATAAGAATGCGGCCGCGGTGACACTGCACTATTGGTTTGCTTCTGATG | F | NotI |
| | P2Ura3 | CATTACCCTGTTATCCCTAGTCGAGCTTCGTAGGAGGGCATTTTGGTGG | R | I-SceI |
| | T1Ura3 | CTAGGGATAACAGGGTAATTAACTATAACGGTCCTAAGGTAGCGATACGG AGATGCTGGGTACAAGTAGC | F | I-SceI/ CeuI |
| | T2Ura3 | ATAGTTTAGCGGCCGCCTATGCTACGAGCGTCGGATTCACCACAG | R | NotI |
| | Ura3Ver1 | GGCACACTGCTCACTATCGCAGGCTGCAACAATG | F | |
| | Ura3Ver2 | CCTGACTCGTCTCGATACTCAAGACCTCATTGACGC | R | |

[F = forward direction/ R = reverse direction]

TABLE 10

List of primers used to construct the pVC vector and quantitative PCR, RT-qPCR.

| | Primer | 5'-3' | F/R | Sites |
|---|---|---|---|---|
| pVC polylinker | Link1 | GGCCGCTAACTATAACGGTCCTAAGGTAGCG | F | |
| | Link11 | CCGAATCGATTCGCTACCTTAGGACCGTTATAGTTAGC | R | |
| | Link2 | AATCGATTCGGATCCCACAATGAAGCTTCCCCGCGGTAC | F | |
| | Link22 | CTAGGTACCGCGGGGAAGCTTCATTGTGGGAT | R | |
| | Lip2Thc | TATCAAATGCGGCCGCTTCGCTACCTTAGGACCGTTATAGT TAACACGATTCGATTTGTCTTAGAGGAACGC | R | NotI |
| | PDX2Xho | GAGTAATGCTCGAGTATCGAAGTCTTGTACC | F | XhoI |
| JMP62 ISceI | 62claS | GCGATATTACCCTGTTATCCCTAGAATCGATTCCCACAAGACGAACAAGT G | F | |
| | 62claR | CACTTGTTCGTCTTGTGGGAATCGAT- TCTAGGGATAACAGGGTAATATCGC | R | |
| LAsp gene | preproLip2 | CGCGGATCCCACAATGAAGCMCCACCATCCTTTTCACAGCCTGCGCTAC | F | BamHI HindIII |
| | Lip2KR | TCGCTTCTGGAGAACTGCGGCCTC | R | |
| | LAspsens | GAGGCCGCAGTTCTGCAGAAGCGAGCCGACAAGCTGCCCAACATTGTGAT TC | F | |
| | LAsprev | CCACCTAGGCTAGTAGGTGTGGAAGTACTCCTGGATG | R | AvrII |
| qPCR Lip2 | LIP2-1 | TACTCTTGGTCAGCCCAT | F | |
| | LIP2-2 | AGAAGGGCACTTGAGGGA | R | |
| qPCR Act | Act4 | TATTGCCGAGCGAATGC | F | |
| | Act5 | CTTGGAGATCCACATCTGC | R | |
| qPCR LAsp | LAsp1 | GCTGAACGACCGAATTGG | F | |
| | LAsp2 | GTGGTGTGCAGCTTGTC | R | |

[F = forward direction/R = reverse direction]

TABLE 11

List of excisable markers constructed.

| Marker | Vector name | Collection No. |
|---|---|---|
| ADE2 | pKS-LPR-Ade2 (direction 1) | JME798 |
| | pKS-LPR-Ade2 (direction 2) | JME799 |
| GUT2-0.5 | pKS-LPR-Gut2-0.5 (direction 1) | JME792 |
| GUT2-1.0 | pKS-LPR-Gut2-1.0 (direction 1) | JME919 |
| | pKS-LPR-Gut2-1.0 (direction 2 | JME920 |
| GUT2-1.5 | pKS-LPR-Gut2.1.5 (direction 1) | JME921 |
| | pKS-LPR-Gut2-1.5 (direction 2) | JME922 |
| LEU2 | pKS-LPR-Leu2 (direction 2)* | JME509 |
| LEU2n | pKS-LPR-Leu2ΔBamHI (direction 2) | JME790 |
| URA3 | pKS-LPR-Ura3 (direction 1) | JME507 |
| HYG | pKS-LPR-hph (direction 2)* | JME508 |

*Fickers et al., Journal of Microbiological Methods 55 (2003) 727-737

TABLE 12

List of random integration vectors, JMP61 and JMP62 series.

| Vector name | Collection No. |
|---|---|
| JMP61-SceI | JME793 |
| JMP61 Leu2nEx | JME794 |
| JMP61 Ura3Ex | JME795 |
| JMP61HygEx | JME796 |
| JMP61 Gut2-0.5Ex | JME797 |
| JMP61 Ade2Ex | JME861 |
| JMP62 I-SceI | JME801 |
| JMP62 Leu2nEx | JME802 |
| JMP62 Ura3Ex | JME803 |
| JMP62 HygEx | JME804 |
| JMP62 Gut2-0.5Ex | JME805 |
| JMP62 Ade2Ex | JME862 |

The invention claimed is:

1. A method for the targeted integration of at least three copies of a gene of interest in the genome of a *Yarrowia* strain including the following steps:

a) cultivation of a *Yarrowia* strain comprising a deletion in at least three genes wherein the deletion is a deletion in URA3, a deletion in LEU2 and the specific deletion GUT2-744 or wherein the deletion is a deletion in URA3, a deletion in LEU2 and the specific deletion Ade2-844 and wherein independent of the at least three genes, the phenotype associated with each of the deletions corresponds to an auxotrophy or to a dominant character for the strain;

b) transformation of the auxotrophic and/or dominant character *Yarrowia* strain with at least three recombinant vectors that include selection markers allowing, for the *Yarrowia* strain, complementation of the auxotrophy and/or of the dominant phenotype resulting from each of the deletions, the recombinant vectors each including:

i) the sequence of the gene of interest, ii) a selection marker, and iii) two DNA sequences framing the sequence of the gene of interest and the selection marker, the two DNA sequences are homologous to the sequences corresponding to the ends of the targeted integration site in the genome of the *Yarrowia* strain in order to allow the targeted integration of the recombinant vector via homologous recombination; and c) selection on minimum medium of the yeasts having integrated the at least three recombinant vectors.

2. The targeted integration method as claimed in claim 1, wherein the genes having a dominant character phenotype are chosen from among:

the hygromycin-resistance gene HPH (HYG), the MDR3 gene, the Kan MX gene and the Tn5ble gene.

3. The targeted integration method as claimed in claim 1, wherein in step b), the targeted integration site in the genome of the *Yarrowia* strain is chosen from among the genes URA3, LEU2, ADE2, LIP2, LIP7, LIP8, AXP, GUT2 or XPR2.

4. The targeted integration method as claimed in claim 3, wherein in step b), the targeted integration site in the genome of the *Yarrowia* strain is chosen from among the genes URA3, LEU2, ADE2, LIP2, LIP8 or AXP.

5. The targeted integration method as claimed in claim 1, wherein the step b) transformation of the *Yarrowia* strain and the step c) selection on minimum medium are carried out separately for each of the at least three recombinant vectors.

6. The targeted integration method as claimed in claim 1, wherein in step b), the transformations with at least the three recombinant vectors are carried out independently and successively with each of the recombinant vectors or simultaneously with all of the recombinant vectors and in that all of the transformations are followed by a step c) selection on a minimum medium of the yeasts having integrated the recombinant vectors.

7. The targeted integration method as claimed in claim 1, wherein the *Yarrowia* strain is a strain of *Yarrowia lipolytica*.

8. The targeted integration method as claimed in claim 1, wherein the *Yarrowia* strain includes four genes having independent of one another a deletion associated with an auxotrophic or dominant character phenotype chosen from among the genes URA3, LEU2, GUT2 or ADE2.

9. The targeted integration method as claimed in claim 1, wherein the step b) transformation is carried out with three to ten recombinant vectors.

10. The targeted integration method as claimed in claim 1, wherein the selection marker is framed by sequences allowing its excision after the targeted integration of the recombinant vector.

11. A method for producing a polypeptide encoded by a gene of interest from a *Yarrowia* strain, which includes:

i) targeted integration of at least three copies of a gene of interest in the genome of the *Yarrowia* strain as claimed in claim 1;

ii) cultivation of the *Yarrowia* strain in a liquid culture medium containing assimilable sources of carbon, nitrogen and inorganic salts in order to allow the growth of the transformed *Yarrowia* strain and expression of the polypeptide of interest; and iii) recovery of the expressed polypeptide of interest from the *Yarrowia* cells or from the culture medium obtained in step ii).

12. A method for obtaining a modified *Yarrowia* strain, which includes a step in which the *Yarrowia* strain is transformed with at least three vectors to produce a *Yarrowia* strain comprising at least three deletions wherein the deletion is a deletion in URA3, a deletion in LEU2 and the specific deletion GUT2-744 or wherein the deletion is a deletion in URA3, a deletion in LEU2 and the specific deletion Ade2-844 and wherein the phenotype associated with each of the deletions corresponds to an auxotrophy or to a dominant character for the strain.

13. The method as claimed in claim 12, wherein the deletion of at least three genes is further associated with a dominant character phenotype selected from among:

the hygromycin-resistance gene HPH (HYG), the MDR3 gene, the KanMX gene, or the Tn5ble gene.

14. An auxotrophic *Yarrowia* strain, which strain includes a deletion in at least three genes of its genome wherein the deletion is a deletion in URA3, a deletion in LEU2 and the specific deletion GUT2-744 or wherein the deletion is a deletion in URA3, a deletion in LEU2 and the specific deletion Ade2-844 and the phenotype associated with each of the deletions corresponds to an auxotrophy or to a dominant character for the strain.

15. The auxotrophic *Yarrowia* strain of claim 14, which includes a deletion in at least four genes of its genome chosen from among the genes URA3, LEU2, GUT2, ADE2, HIS and LYS5.

16. The auxotrophic *Yarrowia* strain as claimed in claim 14, which is selected from the group consisting of the *Yarrowia lipolytica* strains deposited on Feb. 4, 2008 in accordance with the Budapest Treat with the Collection nationale de Culture de Microorganismes (CNCM), PASTEUR INSTITUTE, 25 rue du Docteur Roux, 75724 PARIS CEDEX 15, France, under the numbers CNCM 1-3911 and CNCM 1-3912.

17. The auxotrophic *Yarrowia* strain as claimed in claim 14, which corresponds to the *Yarrowia lipolytica* strain deposited on Feb. 4, 2008 in accordance with the Budapest Treaty with the Collection nationale de Culture de Microorganismes (CNCM), PASTEUR INSTITUTE, 25 rue du Docteur Roux, 75724 PARIS CEDEX 15, France under the number CNCM I-3913.

18. The targeted integration method as claimed in claim 1 wherein the deletion in at least three genes is selected from the deletions Ura3-302, Leu2-270, Gut2-744 or Ade2-844.

19. The targeted integration method as claimed in claim 1 further comprising a an auxotrophic marker selected from the HIS and LYS5 genes.

20. The targeted integration method as claimed in claim 2 wherein the gene having a dominant character phenotype is the hygromycin-resistance gene HPH (HYG).

21. A method for the targeted integration of at least three copies of a gene of interest in the genome of a *Yarrowia* strain including the following steps:

a) cultivation of a *Yarrowia* strain comprising a deletion in at least three genes wherein the deletion is selected from a deletion in URA3, a deletion in LEU2, and the deletion Gut2-744 or the deletion Ade2-844 and wherein at least one deletion is Gut2-744 and wherein independent of the at least three genes, the phenotype associated with each of the deletions corresponds to an auxotrophy or to a dominant character for the strain;

b) transformation of the auxotrophic and/or dominant character *Yarrowia* strain with at least three recombinant vectors that include selection markers allowing, for the *Yarrowia* strain, complementation of the auxotrophy and/or of the dominant phenotype resulting from each of the deletions, the recombinant vectors each including:

i) the sequence of the gene of interest, ii) a selection marker, and iii) two DNA sequences framing the sequence of the gene of interest and the selection marker, the two DNA sequences are homologous to the sequences corresponding to the ends of the targeted integration site in the genome of the *Yarrowia* strain in order to allow the targeted integration of the recombinant vector via homologous recombination; and c) selection on minimum medium of the yeasts having integrated the at least three recombinant vectors.

22. The auxotrophic *Yarrowia* strain as claimed in claim 14 which strain includes the deletion Gut2-744.

23. The auxotrophic *Yarrowia* strain as claimed in claim 14 which strain includes the deletions Ura3-302, Leu2-958, Gut2-744 or Ade2-844.

* * * * *

UNITED STATES PATENT AND TRADEMARK OFFICE

CERTIFICATE OF CORRECTION

PATENT NO. : 8,748,129 B2
APPLICATION NO. : 12/866022
DATED : June 10, 2014
INVENTOR(S) : Jean-Marc Nicaud et al.

It is certified that error appears in the above-identified patent and that said Letters Patent is hereby corrected as shown below:

In the Claims:

In claim 16, column 78, lines 4 through 5, please replace "CNCM 1-3911 and CNCM 1-3912" with -- CNCM I-3911 and CNCM I-3912 --

In claim 19, column 78, line 17, please replace "comprising a an auxotrophic marker" with -- comprising an auxotrophic marker --

Signed and Sealed this
Twenty-third Day of December, 2014

Michelle K. Lee

Michelle K. Lee
*Deputy Director of the United States Patent and Trademark Office*

SEQUENCE LISTING

<160> NUMBER OF SEQ ID NOS: 77

<210> SEQ ID NO 1
<211> LENGTH: 4844
<212> TYPE: DNA
<213> ORGANISM: Yarrowia lipolytica

<400> SEQUENCE: 1

```
acagtatcat taggaaaggg gtgacactgc actattggtt tgcttctgat gatacgtatg     60

aatacgatgg tatcttgata cagagtcttg catacattaa tttcgaaact agagcacagc    120

aacagctccc aaatgagcat tcccctgaag cccatcaaaa ctgcaccaca aatttgatcc    180

catattacca ttttaaagca attgttaaca agatactact gtagaaaact gattaaacat    240

tcgtaacttg cctgtggctc gacttacagc caaatgttcg cggcaaaatt tgaatatttt    300

gcacacttat tgtcccaaaa ccaaataatg ccaacaaaat ccgatatagt gtaggggcta    360

tcacatcacg ctctcatcaa gaatacttct tgagaaccgt ggagaccggg gttcgattcc    420

ccgtatcgga gtgtttattt tttgctcaac cataccctgg ggtgtgttct gtggagcatt    480

ctcacttttg gtaaacgaca ttgcttcaag tgcagcggaa tcaaaaagta taaagtgggc    540

agcgagtata cctgtacaga ctgtaggcga taactcaatc caattacccc ccacaacatg    600

actggccaaa ctgatctcaa gactttattg aaatcagcaa caccgattct caatgaaggc    660

acatacttct tctgcaacat tcacttgacg cctaaagttg gtgagaaatg gaccgacaag    720

acatattctg ctatccacgg actgttgcct gtgtcggtgg ctacaatacg tgagtcagaa    780

gggctgacgg tggtggttcc caaggaaaag gtcgacgagt atctgtctga ctcgtcattg    840

ccgcctttgg agtacgactc caactatgag tgtgcttgga tcactttgac gatacattct    900

tcgttggagg ctgtgggtct gacagctgcg ttttcggcgc ggttggccga caacaatatc    960

agctgcaacg tcattgctgg ctttcatcat gatcacattt ttgtcggcaa aggcgacgcc   1020

cagagagcca ttgacgttct ttctaatttg gaccgatagc cgtatagtcc agtctatcta   1080

taagttcaac taactcgtaa ctattaccat aacatatact tcactgcccc agataaggtt   1140

ccgataaaaa gttctgcaga ctaaatttat ttcagtctcc tcttcaccac caaaatgccc   1200

tcctacgaag ctcgagctaa cgtccacaag tccgcctttg ccgctcgagt gctcaagctc   1260

gtggcagcca agaaaaccaa cctgtgtgct tctctggatg ttaccaccac caaggagctc   1320

attgagcttg ccgataaggt cggaccttat gtgtgcatga tcaaaaccca tatcgacatc   1380
```

-continued

```
attgacgact tcacctacgc cggcactgtg ctccccctca aggaacttgc tcttaagcac   1440
ggtttcttcc tgttcgagga cagaaagttc gcagatattg gcaacactgt caagcaccag   1500
taccggtgtc accgaatcgc cgagtggtcc gatatcacca acgcccacgg tgtacccgga   1560
accggaatca ttgctggcct gcgagctggt gccgaggaaa ctgtctctga acagaagaag   1620
gaggacgtct ctgactacga gaactcccag tacaaggagt tcctagtccc ctctcccaac   1680
gagaagctgg ccagaggtct gctcatgctg gccgagctgt cttgcaaggg ctctctggcc   1740
actggcgagt actccaagca gaccattgag cttgcccgat ccgaccccga gtttgtggtt   1800
ggcttcattg cccagaaccg acctaagggc gactctgagg actggcttat tctgaccccc   1860
ggggtgggtc ttgacgacaa gggagacgct ctcggacagc agtaccgaac tgttgaggat   1920
gtcatgtcta ccggaacgga tatcataatt gtcggccgag gtctgtacgg ccagaaccga   1980
gatcctattg aggaggccaa gcgataccag aaggctggct gggaggctta ccagaagatt   2040
aactgttaga ggttagacta tggatatgta atttaactgt gtatatagag agcgtgcaag   2100
tatggagcgc ttgttcagct tgtatgatgg tcagacgacc tgtctgatcg agtatgtatg   2160
atactgcaca acctgtgtat ccgcatgatc tgtccaatgg ggcatgttgt tgtgtttctc   2220
gatacggaga tgctgggtac agtgctaata cgttgaacta cttatactta tatgaggctc   2280
gaagaaagct gacttgtgta tgacttattc tcaactacat ccccagtcac aataccacca   2340
ctgcactacc actacaccaa aaccatgatc aaaccaccca tggacttcct ggaggcagaa   2400
gaacttgtta tggaaaagct caagagagag aagccaagat actatcaaga catgtgtcgc   2460
aacttcaagg aggaccaagc tctgtacacc gagaaacagg cctttgtcga cgaagctcta   2520
aagctgaaac gggacatcga aaagttggag aagtcaatct ggaaactaca cgtagaaaac   2580
agacaccatc tccaacaagt acaggacttc aaatttgcac tgaagacatt ctgtgggtgg   2640
agccataagt aacaatcgcc tgctccagga acttaaaaaa gaggcattat aggccccttc   2700
atctgaatat tctttgagta ccaactgccg ccaactcccc aatcgttaat tagtgttatc   2760
tattctatct atgctattag cacatattta tcatgtgctg ctgttatgta cgggttcaat   2820
atacaaatgc ttagtcctca aacaccttca taggtgggtc gtcttcctgg ccaaatcgaa   2880
ttctcatgat ttcaaacacg aacagaccga tagacgtaga cggaagcgca ctgagggtcg   2940
tccagccaca accatggtat aggtatctgg gccaactcaa ccgcagaccc tttcggatgt   3000
tattggctgt atgcagagtc tcaacgtagg ctcggtagta gagatggata cccgggaaga   3060
ttctgtatct aagagtagta aaacatctaa tagaaaagtt gacggtctta ctccatccct   3120
taccaaactt cacaagaagt gaatgcgttc tgggaagagt ctcctccagc gtttcagaca   3180
gttccaccat aagagggttt ctgtggtgaa tccgacgctc gtagcataga aatgttgact   3240
ggaaaggaga ggcgggactg gcctgatgtt ttattcgctc tccaagtttg ttctgtgtct   3300
tttgctcctt ggatcggtta gcttccagtt gttttcttgc gtcaatgagg tcttgagtat   3360
cgagacgagt caggtagatg ccctgcagct tctgaagagg aaactgaacc acatgcagtg   3420
agatggtggc tgctgctcca gctacaagga tgctgaaagg tgctaggacc ttgttgacga   3480
tgctttttcc attctcatca aagcctgaag gatgttcctt gagacgatca gcatacagcc   3540
acttggcata ggacctgtac cacgatccct taaccatttc gaacgtggca aaaaagaccc   3600
caaaacccag actctctttg acaactgaca acgtaaagcc agcaaagaca cctggtgcac   3660
ctgtttggcg caacttctcc attccatagg accacataga gggcaactgt ttggtcttga   3720
gcacttctgc tatcgaagaa cgcctgtaga tggcgtcgat tggtgctgca gctactgcct   3780
```

```
gggctgctcc agcgactgct ccggcacaaa acgtctgttt gaacgtgtat cgatgaggca   3840

tgagttcatc gatgatgtat ttcacatgcg agccgtccat tccctgggta tcataccatg   3900

atttccttag cagcagttgt cgttggtgtt cgtcttcttc atcctccttt tgtcggtctt   3960

tctctgattt gaataatggt agacatccca gatatgtgga gtacaatacc agtcctacgg   4020

ccgagttcgc caataagggg ggcagcaatt gatttggaat aaaaccccag ccatgctgtt   4080

tgactgcgtt ggcaatcaga gccggactgc tgtgtgtttt gaagctccaa ggtttgtcgc   4140

tgtttggaga cagcgcccgt ggaagcgcta agtagtcgac tctggtaggt cgaaagagct   4200

tgacaggcac acggatgtaa aatgtgaaga gctgggatgc gagcgcccga gtaccggccg   4260

tcgtagctcc aataatccgg gccgagcttg gtttccatgc ttcgttattg ttttcgtgcg   4320

gttcggtgaa ttccggaacc tcgggcagaa atcccggaac gtcgccgggc tcgattttct   4380

gcatgaggcc tagaaacact ctccagtgtc gcgggacgtg aggaacgggc ttctatctgc   4440

tgagcgatat caggtactgg tcgtgcttgc ggttgtccag agatccaaaa cttttgcgat   4500

gcgtcaggga cgcacagttt accgacaacg gaggagtgca aaacgtgggg gaacagggca   4560

gtttgtgtgg gtgggtcggc gagtccgaat gatgattttg tatcgttaca gattgcgtgg   4620

ggtggagatt aatatggctg ctcgaaaatt gctcgtgtcg cgttactgag aggcagagta   4680

catgtacgcg agctctcctg tgtctactcc ttcacctctt taatgttgct gtacatatac   4740

gcggtatgat agatgtggtc aggtggtgga tttgggaatg aaggtcggtt tgggctcggt   4800

agtggtaatg agtgtcatgg gtgaggctta agtggcgaga gatc                    4844
```

<210> SEQ ID NO 2
<211> LENGTH: 968
<212> TYPE: DNA
<213> ORGANISM: Yarrowia lipolytica

<400> SEQUENCE: 2

```
gaattccgtc gtcgcctgag tcatcattta tttaccagtt ggccacaaac ccttgacgat     60

ctcgtatgtc ccctccgaca tactcccggc cggctgggta cgttcgatag cgctatcggc    120

atcgacaagg tttgggtccc tagccgatac cgcactacct gagtcacaat cttcggaggt    180

ttagtcttcc acatagcacg ggcaaaagtg cgtatatata caagagcgtt tgccagccac    240

agattttcac tccacacacc acatcacaca tacaaccaca cacatccaca atggaacccg    300

aaactaagaa gaccaagact gactccaaga agattgttct tctcggcggc gacttctgtg    360

gccccgaggt gattgccgag gccgtcaagg tgctcaagtc tgttgctgag gcctccggca    420

ccgagtttgt gttcgaggac cgactcattg gaggagctgc cattgagaag gagggcgagc    480

ccatcaccga cgctactctc gacatctgcc gaaaggctga ctctattatg ctcggtgctg    540

tcggaggcgc tgccaacacc gtatggacca ctcccgacgg acgaaccgac gtgcgacccg    600

agcagggtct cctcaagctg cgaaaggacc tgaacctgta cgccaacctg cgaccctgcc    660

agctgctgtc gcccaagctc gccgatctct cccccatccg aaacgttgag ggcaccgact    720

tcatcattgt ccgagagctc gtcggaggta tctactttgg agagcgaaag gaggatgacg    780

gatctggcgt cgcttccgac accgagacct actccgttcc tgaggttgag cgaattgccc    840

gaatggccgc cttcctggcc cttcagcata acccccctct tcccgtgtgg tctcttgaca    900

aggccaacgt gctggcctcc tctcgacttt ggcgaaagac tgttactcga gtcctcaagg    960

acgaattc                                                             968
```

<210> SEQ ID NO 3

<211> LENGTH: 1698
<212> TYPE: DNA
<213> ORGANISM: Yarrowia lipolytica

<400> SEQUENCE: 3

```
atggactcga aaacaattgg tattcttgga ggaggtcagc tgggccgaat ggtcgtggag     60

gctgcccatc gactcaacgt caagactgtc attctagacg cccccaactc tcccgccaaa    120

cagattcatg ctggagagca tgtcgatggc tccttcaagg accctgccga cattgctaag    180

cttgcctcca agtgcgacgt cataaccgtt gaaattgagc atgtgaacgc cgacactctg    240

gccgatctcc agaagactgg tgtcgaggtt cacccttctc ctgagaccat ccgaattatc    300

caggacaagt accgacagaa ggagcacctg atctcccacg gcattcccgt tgccgaatcc    360

tacgaggtca ccgagtctac tgaggctgcc cttgtcgttg ctgctgaaaa ggtcggctat    420

ccttgtgttg tcaaggccaa gactcttgct tacgatggta gaggcaactt cgttcttaag    480

ggtccagaga atgtcaagga agctcttgag ttcctctccg accgaccttt gtacgtagag    540

aaatggtgtc ccttcgtcaa ggagctcgct gttatggttg tccgatctac cgacggaacc    600

actgttgctt accccaccgt cgagactgtt cagaaaaaca acatctgcca tactgtctac    660

gcccccgctc gagacgtttc tccttccacc ctgtacgagg ctcagctcgt tgccgagaac    720

gccattaagt ccttcactgg cgctggtatc tttggtgtcg agatgttcct gctcgaaaac    780

ggcacgattg ttctcaatga gattgctcct cgaccccaca actccggtca ttacacaaca    840

gatgcctgct ccacctcgca gtttgaggcc catgtccgag ccattcttgg tctgcctctt    900

ttccccgaga tggcccagat gcgaacagca gacactcatg ccattatgct gaacattcta    960

ggaggtgaca agcccgacag cgagcttgag tactgcaagc ggtcactttc cgtacctggg   1020

tccaccatcc atctctacgg caagaccacg agacccgagc gaaagatggg acacatcaac   1080

attgttgcta gcagcatgga cgaatgcgag cgacggctgg ccaaaatatc tggagaggac   1140

atcgaggagg caccaaagac tgtcgagggt gtagcaggaa cctctaagac ccccctcgtg   1200

tctatcatta tgggctcgga ctccgatctt aaggtcatgt ctgccggagc cgacatcctg   1260

cggaaatttg acattccctt cgaactgacc attgtgtctg cccaccgaac cgcccaccga   1320

atggctaaat ttgccgctga ggttgccagc cgaggtgtca aggctgtcat tgccggagct   1380

ggaggagccg ctcaccttcc cggaatggtt gcctcggaaa ccactctgcc agtcatcggt   1440

gtccccgtta agggctcctc tctggacgga gttgactctc tctactccat tgtgcagatg   1500

cctcgaggca tccccgtggc caccatgggt gtcaacaact ccaccaatgc tgctctgctg   1560

gccatccgaa ttctggctgc ttacgacgcc accctacaca ttcgactggc cgagtacatc   1620

aagaacatgg agaaggaggt tcttgccaag gccgacaagc tcgagaccat tggatacgag   1680

cagtacctca accaatag                                                 1698
```

<210> SEQ ID NO 4
<211> LENGTH: 1839
<212> TYPE: DNA
<213> ORGANISM: Yarrowia lipolytica

<400> SEQUENCE: 4

```
ttatttgtcc ttgggggtaa ggcccatgga gtagaggtac tcgacaccgg tgttgaattc     60

ctgctccttt cgagcctcgt cccactggag ctccttggcc atgatctcaa tgacctcagg    120

gagagcctcg taggcggcag cggcgttaag gaaagcaaga cgagttcgtc gagcaaggaa    180

gtcgatggcg gtggtggcat actcgtactt catagagtac ttgcactcgg catcgaggta    240
```

```
ggggtagggg tacaggattc gcttaccctt tgtgagagta gactggggga tcacaccggg    300

ttcgggggtg ggcatctcag caagagaagc aacggtgaaa gctcgagatc cgtagttctc    360

agaaaggtgc ttagcaacct cggggtcaag gtcctcctgc tggatcagat caatgtaagt    420

gagaggagtc cagtccttag caccgatgag cttgacgtct cgggtgacgg ccttggcgga    480

gatttcaggc ttgagaccga acttggcaat gcaggcatcg acagtctcct cagccatctg    540

tcggtaagtg gtccactttc cgccagcaat ggtgacaaga ccagactcgg agtaggtgat    600

gagatggttt cggacaagag actcggtgtt cttggcgtgg gggtcccgga caaggggtcg    660

gattccggac caggcggcca gaacgtcctc tcgtcgcaca tcaaccttgc cctcaacgta    720

gtgtcggacc tcgttgagaa tgaagtcaat gtcctcctcg gaggggatag ggttagcagt    780

gatcttggta ggctggtcag tagtaccggc aagggtgttt ccctgccagg ggaggaagaa    840

gataactcgg ccgtcagaag tagcggggtc aaggagtccc atcttcttgg gggagtagta    900

accggggaga atgatgtgaa caccggagga aggagcacag atctccttgg tgttcttgtc    960

gtccatctgt cgcagagagt cagtgaaggg tccagtagca ttaacgacac acttggcctt   1020

gatgttgaag gatccagcgt ttccgtcagt atccttggca acaacaccgt tgagctggcc   1080

attggcgccc ttggtgagct cggtgacctc gcaatggttc aggatggtgg cacccttctc   1140

aacagcagtc ataataagag aaacgttcat tcgagagtcg ttctgggagc catcatagta   1200

gacaatggcg cccttgagct tgtcatcgga aagcatgggg aaggcatcga gagcacggga   1260

tcgggagagc atgtaagagg actcgaggtt ctgtcggccg gcaagcagat cgtagcactt   1320

gacacccatc cagaagtagg gaagctgcca ccaggtgtag acggggatca tgatgggcag   1380

agcaaaggtg aggtggggag caatgtcgag gaagaccttt cgctcgtgca gggcctcctt   1440

gaccagctcg tactggttgt agtcgaggtt ccacacagcc ttctcgaggt atcggacacc   1500

tccgtggatg agcttggtgg atcgggacga ggttccgcag gagaaatcgt ctcgctcgac   1560

cagagcaacc ttgaggcctc gtgtgacagc gtcgagggcg ataccggatc cggtagctcc   1620

tccaccaaca acgacgagat caaactcctc ggtcttcatc ttctcgagct gggcggctcg   1680

agaggggggc tcggcggcca cggggggcac tgtgaatttg tgcttcttgt ggagctcctc   1740

ctgggcctgg gcaggcacag acagggcgac ggctccagcg ccagcggctg ccacggcggc   1800

ggcagcagcc cacgcgggtt ttcgaatggt tctgaacat                          1839
```

<210> SEQ ID NO 5
<211> LENGTH: 5304
<212> TYPE: DNA
<213> ORGANISM: Yarrowia lipolytica

<400> SEQUENCE: 5

```
gatatcggta gcaaacagac acgaagaaga ggccttggag aatttggaaa caacatccat     60

tcgtgctcct tgtttctgct tgccatgcaa atgcaacagg gggataccgg gctgcagagt    120

tcggaaggtc tcgtagacgt atcgcacctg ttttgatgaa ctgaagaaaa cgatgatctt    180

gaacttggtg tgtgttctca ggaaacccca cagtgtgtcc agcttgtctt gcagctccac    240

gcagacatag ttctgttcga ggttcttggg tgtgctggaa gtggtgtccg ggttggcgga    300

gatgtacttg ggtcggcga gtgacaaacg ggccagatca ctgacgctct tggtctgtgt    360

tgcgctgaaa agcagagtct gtctgtccac aggcaggttt tccaaaatgg catccatggt    420

cttcttgaaa cccatatcga ggattcgatc ggcctcgtcc agcaccagca tcttcacgtt    480

agaaagatca aacccgctag tttggtccat gtgttgtaac agtcgtccgg gtgtacaaat    540
```

-continued

```
gagaatgttc agcttggcca gtcggtcagc ctccatggca acgtcctttc ctccaataac     600
caaaccagca gagaagctgt gacaacggcc gatttttcgc agaacctgga aaatctggac     660
cgccagttct cgagtcggac taataaccag ggctcctaaa ccatccacat cactccactt     720
gtttcgaaac aggcactcca acacaggcac cagaaacgcc agagtcttac cacttccggt     780
acgcgctgct ccaagcagat cgtggccttg cagagcggga gggatggccc gcttctgaac     840
atcggtacag gtgacataat gtgaattttt tagaccctca atagtagcct cagacaaggg     900
cagctcctca aacttggaca cctccttgtc ggcctcgtcc tctccaaagt tgtcgacgcg     960
ctcctgcagc ttggagagct tctgtttgtg ttcctctcgt ttgattttac gaggatcggc    1020
tcgtttcttc attttcgcca tatctcaagc tgtcggataa atttcttgga caaaaaaatc    1080
taacttttcg tgcgccttca cttttatcag tctgaaaatt acacatgcat gcagcttgga    1140
gtatggaggc gacagaggtg catgccagag tgcatgaatt agggcaacgg gggtgtgaag    1200
aagggcgcaa aagatgtgac gacggtgcaa gacgacggta tactgcagac aaggtctttc    1260
actgcaaaac tcctggttaa atcgtgggtc ccgcgtctcc gtatcatatg actttgggtc    1320
acgtgactgc aagattttta aggtttcgaa ctcccaaatt gagtcacgtg tcgtctctct    1380
gcaacatgag gtatcgtaaa ttaggaatga ctcgacctga caggccatca aggaccctga    1440
tgcaactctg aaattagagg gaggaggtaa tgagaaacag tgctggattg tggtgagaca    1500
ttgaagcggg attggttaac ctgtttcttt tttgtcgttt gctcttcatt attgcgattt    1560
ttgtagtcat ttgattagat cagatcagca gtcccctcat gctgtcgttg atgggcgcgt    1620
aatcagtgta acgctttgaa tgaggatggt gtgagtaata ctggtttcat tggggggggg    1680
gggggggta ctgttactcg aaaaacaaat catatgcatc tctgaacgtg ccggggtgtg    1740
gcatgtttct cgcttcgaaa aataaatgtt ggctgttcca ggcttgtctc agacctgcaa    1800
gaatcatact ggcgtaatct ccgccaggtc tggtcaggaa caagagagta aaagaaatgt    1860
ttgagtctcg gctttcacat cctcggcact agataagcag caatatcaat gtcacattgc    1920
ttgcttgtgc aggtcagggg gagggggatg tatatgatac aagcaggttc gcatctacag    1980
aatctacagt atgtatctga tgatagcctt acacagcgca cgcagatgta gtttttgggt    2040
tgaacagtgt cagcggaagc ggcgtagtgg ggtactgtag tacagaatca acggaatgaa    2100
gtttacaact gcttctgtta ctgtagcctt tcactgttca aatgataacg ttggagaaga    2160
gtgcaccctc tgttagatag gattacagtc cagacacaca ttggcaccga agtctgtagt    2220
caaacattgg tctcagttgg tgtaatgaca ttcaatagac tgattctgca actcctacac    2280
cttgcattgt acacccgaga ccccttgtac ggcccgcatt tctccttcac atgtcggcat    2340
gtgtcttgtc tgtagccact tcaatgggat gcagtattag cactgtcgga cacacctcag    2400
tcaatgggaa tggaatgcca tgctcctagc ggctcattgt ttgctaggaa atacagttaa    2460
tagcacagat catagagtct aggctctata cgtcttagaa caaccattat ttgtttaaac    2520
gacaacttgg taagcgaatt acagtaagta gctattgttt ctatctctgt cagtgttcgg    2580
ataagtcctt agatcaccat actcaaagtg gtacgtttcg tcgcatcgga cgagaagtgt    2640
gtctatcacc gtttcttttt gccgctctca tttttgcggt cggaataatt actgtggacc    2700
ctcggcgccg accgttttgc agggctcatc aacctaaaac ttctccgagt ctgtgccttc    2760
aggtgggcat agttgatggg tgttttgaag ttaatagtgg ggaagaacta tggcaaacaa    2820
gcagatgcag gcaccttgta actgcagacc ggttcttgtc taccgactcc gctgcacctg    2880
tgccgcggta catgtcgtca caggctgcgg ggttcggagg ccccccttgca acctcctttg    2940
```

-continued

```
atagttgcta tggccccaaa gagttatacg agatagaccc acagatctac ttgactgttg   3000
tcacagaacc tgctaggttt gcttattgta cccgctttgt agctactgta caacgacaac   3060
gtctaaaatt gagacgcgaa caaactccag atgcagaacc caaacctctc tctcagagtt   3120
tcgagtgctt ctacctcaca gtaaagtgga ggtggacctg caagggaatt cagtcacaag   3180
gccccgaatg tctccgaaac tccaatcgga ccgtttaaac agactaatat cacgtcattg   3240
attgatatta gcatccggca agagccgcaa ggttatctcc tcaccaatga gcctgttgta   3300
cggctcattc cgcatctgcg gctgattcag tttcgagtgg ggatggtaga cttcattgca   3360
gcattcctaa ccttctactt ggtccgtgga gatgtcatgg acatcgattt tgggctgaga   3420
agccttttga cgatgtcgat atcactgacc gctaatttac tctggcagtt tctccggctc   3480
tcgaggcatc gtcgatcacc aaacactatc tgctagtcta aatgtccgac acgacagctt   3540
ttgatcgccg tgaacggcgc agacctcatg caccatgcac cagggccaaa tcaattacgg   3600
gtcgcttagc gttgcagtcg gggcattatg gtggaagttc cgatacggca cagacacatt   3660
ccatagtggg ggattggat tataaaaggg ccatagaaag ccctcaattg atacccaagt   3720
accagctccc ctcactatga agctttccac catccttttc acagcctgcg ctaccctggc   3780
tgccgccctc ccttccccca tcactccttc tgaggccgca gttctccaga agcgagtgta   3840
cacctctacc gagacctctc acattgacca ggagtcctac aacttctttg agaagtacgc   3900
ccgactcgca aacattggat attgtgttgg tcccggcact aagatcttca agcccttcaa   3960
ctgtggcctg caatgtgccc acttccccaa cgttgagctc atcgaggagt tccacgaccc   4020
ccgtctcatc tttgatgttt ctggttacct cgctgttgat catgcctcca agcagatcta   4080
ccttgttatt cgaggaaccc actctctgga ggacgtcata accgacatcc gaatcatgca   4140
ggctcctctg acgaactttg atcttgctgc taacatctct tctactgcta cttgtgatga   4200
ctgtcttgtc cacaatggct tcatccagtc ctacaacaac acctacaatc agatcggccc   4260
caagctcgac tctgtgattg agcagtatcc cgactaccag attgctgtca ccggtcactc   4320
tctcggagga gctgcagccc ttctgttcgg aatcaacctc aaggttaacg gccacgatcc   4380
cctcgttgtt actcttggtc agcccattgt cggtaacgct ggctttgcta actgggtcga   4440
taaactcttc tttggccagg agaaccccga tgtctccaag gtgtccaaag accgaaagct   4500
ctaccgaatc acccaccgag gagatatcgt ccctcaagtg cccttctggg acggttacca   4560
gcactgctct ggtgaggtct ttattgactg gcccctgatc caccctcctc tctccaacgt   4620
tgtcatgtgc cagggccaga gcaataaaca gtgctctgcc ggtaacactc tgctccagca   4680
ggtcaatgtg attggaaacc atctgcagta cttcgtcacc gagggtgtct gtggtatcta   4740
agctatttat cactctttac aacttctacc tcaactatct actttaataa atgaatatcg   4800
tttattctct atgattactg tatatgcgtt cctctaagac aaatcgaaac cagcatgcga   4860
tcgaatggca tacaaaagtt tcttccgaag ttgatcaatg tcctgatagt caggcagctt   4920
gagaagattg acacaggtgg aggccgtagg gaaccgatca acctgtctac cagcgttacg   4980
aatggcaaat gacgggttca aagccttgaa tccttgcaat ggtgccttgg atactgatgt   5040
cacaaactta agaagcagcc gcttgtcctc ttcctcgaaa ctctcaaaca cagtccagag   5100
gtcctttata gcttgatctg tatccagata gcctccgtaa ttggtgtgtg tcttcaaatc   5160
ccagacgtcc acattggcat gtcctccact gataagcatt tgaagttcat ctgcgttgaa   5220
cattgagacc cacgaagggt caatgagctg gtatagaccg cccaagaatg catctgtctg   5280
tgttctgata ctggtgttaa gctt                                          5304
```

<210> SEQ ID NO 6
<211> LENGTH: 2092
<212> TYPE: DNA
<213> ORGANISM: Yarrowia lipolytica

<400> SEQUENCE: 6

```
acgcgtgtga tcgcgagcga gtaacgtcca ccagtcttct gggagcccct ttcctccaaa     60
aggcctgaca ttgacgcttt aaaaaagttg acatctgaaa caagcagccg ttgccggggg    120
tctcattggt ataagacagg ataccgttga ttcaccggtc atggttcacg ctagtttgca    180
accccccccc cgcagagatg caacctccac ctaaggaata tcaagacaaa agactcaagc    240
acaagttgaa gcatggcaca agctccagcc cacatgccaa ggttcacagg tggatatatt    300
gactggacct acattctttg tctgcgtgac agtttcgaga atgtgaagat acccaaagtg    360
cggtgattat gatgctggca gggcctccca gggtctgttt caaatcgcta caaccacatg    420
gctggattat ctactcattg cagatcagga acactttctg ttggctcccg cgtgcagata    480
ttatcatcta actagtagct aaagtcgcgc tagcgcctct ctagcacagt catgcacgtt    540
tagatctgtt cgggtcatgt caggtatacc tgtttattgg tatattgagg ggattaccag    600
ttgaacaagc atgacggctg tggcggtaga tacacaaaga gaacgacttc tataagaggg    660
actattcttg ccctctgggt catcatcaag cagcagcttt ccacccttct ctctcccaat    720
ggtatccctc tctgctcgaa tcaaagactt tttttcggtc ctcctcctcg gagctgcaac    780
catcactccc tccacacaga ccgcaggcgt gtctcaaggg ttctatgatt ttgctcggga    840
ctttgcccat ctgtccaaca ttgcctactg tgtcaatgct cccatcactc cactgaaccc    900
ggacttcacc tgtggcaact cgtgcaagca ctttccggaa attgagcttg tgaagacatt    960
tggaggcaac ttcttcaaga cctccattac gggctacctg gctgtcgatc atgtcaagaa   1020
ggagaagtac gttgtcttcc gaggaacctt ttcgctggca gacgcgatca cggacatgca   1080
gttccagctg tctcctttcc tggtcgatgt gcctgccctg aacactttct cagctaatga   1140
caccaccgca gaggcccaga cgcactgtga gggctgcaaa attcacgacg gcttctccaa   1200
ggcctttacc gagacctggg gtaacattgg tgaggatctg cagaaacacc tggacgctaa   1260
cccggactac cagctgtacg tgactggcca ttctctggga gctgctatgg cccttcttgg   1320
agctacttcc atcaagctca agggctacga tcccattctc atcaactacg gacagccccg   1380
agtcggaaac aagcccttcg ctgagttcat taacaagttg tggtttggag aaggcaacgg   1440
tctggaaatc acccccgaga gaaagctgta ccgaatgacc cactggaacg acatctttgt   1500
tggcctgccc aactgggagg gatacaccca ctctaacggt gaagtataca tcaacaaccg   1560
gttcatcaac cctcctctca aggatgtcat ctcttgtgct ggaggcgaaa actcgaagtg   1620
ctaccgatcc tcgttcagcc tgctgtccca gatcaatctg ctccaaaacc acctggctta   1680
cattgattac attggatact gcgctctgaa cattggtcga cgagagcttg ccgatcagga   1740
acattacact ggtccttatt actatggtca tcgatctgag gaggacttta agaagttggg   1800
cttggagcta tccaccccac aagttgagaa ctgaacgagt tgacatgcct gcactactca   1860
acaactaact acttgtagtc gtcactttac tattatctag ctgtaattgt atattaatat   1920
atctaacgaa tataacagac ggctatagag tacaaccttc atcatacaac tcatgactga   1980
gttcatttcc cgactaatga gactgacaaa tgttgggctt ggagggttgt tgggcttgga   2040
ggactgttgg gattggagga ctgttgggct cgaagaggtt gatgtgtttt ct           2092
```

<210> SEQ ID NO 7

<211> LENGTH: 3478
<212> TYPE: DNA
<213> ORGANISM: Yarrowia lipolytica

<400> SEQUENCE: 7

```
tcctcgtcat aatgacgata aaatttatgc tatggtataa aatcactgtt ttacgtcagc     60
gctgcccagc acaggtattc acatgtagct atgacaaacc acacggcata tgaacatgcg    120
ataaggcaac aggaacattt ttttcagttg ttcctctcga atagggtcac tttatgctag    180
gcttgtacta ttaacaactc ggcacctgca caagtctgaa ccccgacttg caacgaattg    240
tggggtgcga gagggactac tacaggtaca acctgaacag taaaagaggt agttgagcag    300
gcaacataac gtgatatcaa ccaggccaca ttagagaccc caagctgcgg gtgatctcta    360
taggtgtcct tcgatatcac tcatcacttt tttggagtgt tggtcgaaag ggatgcacca    420
ccggttacga gtacctggta aatttttccc gaggctgaca ttcctagatc agagttgtgt    480
ctcattgata agagaagtga actacttgta gcagtgacag ttccctatac tgcttttcga    540
actgtacgag ggcacacacg gcctccgaag aagcaaaagt gaacgccgaa gaagctcatt    600
cgaggctatc agtgttctaa agatgttgat ctccttgtgc caatatgaac ggcaccagct    660
ggttaatgtg gggttgagag tgcggaacct tgttcgaagg cccattctac tctgtacacg    720
atttgcaacg gccagcgaga tatcaatgag tacggcgtgt atatgtctca gggagaaaaa    780
aactccttcg gggtacggaa cctcaaacac cactgagctc ctaacggctc tagaggagag    840
tcctcttgag cgattgagtc actgaggagc agggttccat caagtcgcag ataaagaaac    900
aagcaaacaa cgatgccgtg tatctcacac ccacctccaa gacccttgga agaccagcca    960
tgaaccttag cttccaccaa agcctgaacg gcacgaggcg atcgtggcaa tccacgtgca   1020
agtgtaaatc agtgtttaat ctcgaagctt gcatggttta gcagggggcc gtcctatagt   1080
aactgcacga tagcgccctg ccaagcgatg ccacgacggt gccaagaaac atggaatgtc   1140
ctagttttgg agtggtgcgt tgcggattat gttagcgctg tgtgttactg gggaataga    1200
gatacgctcc ctcgcagctc agacgtcaag tgcacccata tactcggtcg agacccattt   1260
ctcgtccttg tccaaagttt gaccctggct aaggcacatc agggcctatc gtgataaaca   1320
agtactgtac atctgtatgt acgtgggggt actgcgaaaa ctgataacgt tgaaatacaa   1380
tggcttgaaa tcggtgtcgg tctgagtgaa ttctagcgat tgtacggcaa gatatatatt   1440
ggagtctctc aataacatat tgcttttgga tcaatggttt tgttggcttc tgctggacca   1500
aatacacgtc ccttggtgag acaaacaaac acaccacgcc gttatcgccc accttatttg   1560
ccttctaata ccgcactata ttggaacttt cgactcattg accatgcatc tcaccagagg   1620
caatgactga ggaccaggtc gaagtagctg gcggaaaagt ggttgtacca gaaaacagat   1680
tcacaagtac ctataaatca ctttgtgtgt gaggactctg gaactgctca cgagtggttc   1740
caggctactg gtagttctat tcgagctcca aagcacatta agttacgctt ggtgaactat   1800
agcttctggt cctctgcttg caatgaagct gtgggtggag taaacggtgc cgcttaatac   1860
agggatggtg cgtgagatag gagatttgga gccgtctact ctgtcggcca acgacataaa   1920
tagacccccct cagtcacctt agacacagca gaattccacc agatcagctt ccaattctaa   1980
agatgcagtt ctctcttgcc acccttacca ccctcttggc cttcgttgcc gcagcccccg   2040
caaacaaggg atttgttcat gcccctatca agaagcagtc cctccaggcg gcccagagca   2100
agatccccaa ctttgcctcc tccggcccca tcactgccga gctctacaat gagctcatgg   2160
cttaccaggt tcaaatttct cttggtggtc agactatctc tgccagcatc gataccggat   2220
```

```
ccgagattct gtgggtttgg gagaacgact ctattgcttg ccaggttgac cagcaggact   2280

gcgacactga cggctcttac aaccccaaga agagttccac gagcaaggac accggagtgc   2340

ctttcaacat caactatggc aagggacatg ctgatggtta cctctacact gataatgctg   2400

tcattggtgg agcttccgct cctggtttca agtttggtgt caactctggt gatctcagct   2460

ccggcggctt ctccatggtc ttcggtatcg gtgtgaacag cgacgcctct acttccatct   2520

ctgctcagct ccaaaagtcc ggcgagatct cccgaaacct ttacggtatg tcattcagcg   2580

acgccaacct tgctggcacc agcaacgaca actctgagat cacctttggt gctatcaaca   2640

ctggtcgata cactggctcg cttaagacca ttccccgagt tgcgacccaa ggcggatacc   2700

agcacttttc cgtttctgcc tccggaaagt ttggagatgt cgacctcttc gacaatgacc   2760

tcgtcattct agactctgga accaccatga cttacctcaa gtcggactac tacaacgcct   2820

tcctcggcgg cctcgaggac cttgatatca ccctcagtga ctactctgga ggatggcacg   2880

gatacccttg ctctgaaaac tcgaagatca acttcactta caacttcagc ggtaaggaaa   2940

tcactgtgac tggacacgac ctggccattc ccggcaacgc tgtcaactcc aatgttgact   3000

cctcagtgtg tttcatgggt gttgacgatg gtggaaacat gaacctgttc ggtgacacct   3060

tcctgcgagc catttactcc gtctacgatc tcgagcgaga tgaggtctct attgcccagg   3120

ctgcccatgg caagcccgac aactacgtgg tcatcactgg tgatgtcccc aactagacta   3180

ttattatcta gcatttcttc tacaagaagc cttatggcaa ctatataatt taattcatta   3240

aaaatgttct atgctaaatg gtgaggcagt gattcaattg caggttcaac attgttggat   3300

gcaattcaag ttttcaatgc gcgcggtgtt gtattcggcc cagaggaggt ccaaagacga   3360

gtggaacatg atcgccaggt ggagcctttg gactgaaata atcaaagagc tcattcaatt   3420

ggttttgtag ctgctcaaac tccttttgaa cggtctcaag ctgcttctcc accccaca     3478
```

```
<210> SEQ ID NO 8
<211> LENGTH: 2966
<212> TYPE: DNA
<213> ORGANISM: Yarrowia lipolytica

<400> SEQUENCE: 8

gttcgtgccg agctcttgtt ctaccgattc agacgtacgg tcgagcttat tgaccgaaag     60

aacgaggaca gacgcaactc agcggacggc tccgagcctg tttccatcac agaggacctg    120

cgggaattgt tatctcggaa agtcattgtt gtgcgtgagg gtgagcgtcc tgaaggcgta    180

atgggtgggt aggtaatgca gtttgcatgc atgaagacac taaacaagcc aaccatacag    240

cagaagtatg tagccttgca catgatttat tgacaggcca cccaaacagg cgtatgtata    300

gtactgtacc ttcagtagac tattgtagct aacatgtcgt tgcgtggcgt atgtaccaag    360

ccacagaaat tatgtcagag ataaggtcgc gacagttaga gcagcaacgc gtggagagtt    420

tgggttttgg gttacgtacg tagagccgtt tgatagatgg tacatccacc ggctagcgga    480

acacagtgtc aagacaagcc tgcaacacag tcataatatt tgcgatattc aggcgtatca    540

ggtacaatct gaggtgtctc acaagtgccg tgcagtcccg cccccacttg cttctctttg    600

tgtgtagtgt acgtacatta tcgagaccgt tgttcccgcc cacctcgatc cggggtccta    660

tgcatccctg aaacattgat tggaaattaa catatgagct gcgtgctttt tgcattcaag    720

ggcgcagctt atcttgtatc cttaattaca catgacctct tgagcgccac ggtacattcc    780

tggcgtcagt tcggtggagc ggacactttt ctctcctttg tctgacatgt tggttaagtt    840

gtagtccagg gacacaaggg gttccaacgg cagtggcagc ctaccccacg ctacccacca    900
```

```
ctggccctgg tctaacttcg acgatcggca tcagggttca tggataggtg gtgtgattta    960
cgatgtgatg gacaatgtta gagagatccc actacttgta gtcaggccat cttttacgta   1020
cgcactgtac catgatgtca atggagtatg atgaaccgac tttgagagac tcacatctgc   1080
acaacaccat gtttcagcgg aatccgactt ccaacccaaa cccaagcccc tgtcagatat   1140
cgtgagaagg cacggcacca actaatgcac acactccacc tgtattgcac caagataatg   1200
agggcatcgt cttggcgcgt cttggcgaga gccgtgtttc gtgacgcaat cagagcagtt   1260
tctggatagt atcttgtcca gaaacacgat ataaacccca tcgacgggcc cgttgaagag   1320
caccaaccca ctatccaatc ctccaatcca acaatgaagc tcgctaccgc ctttactatt   1380
ctcactgccg ttctggccgc tcccctggcc gcccctgccc ctgctcctga tgctgcccct   1440
gctgctgtgc ctgagggccc tgccgccgct gcctactcat ctattctgtc cgtggtcgct   1500
aagcagtcca agaagtttaa gcaccacaag cgagatcttg atgagaagga tcagttcatc   1560
gttgtctttg acagtagcgc tactgttgac cagatcgcct ccgaaatcca gaagctggac   1620
tctctggtcg acgaggactc gtccaacggt atcacctctg ctcttgatct tcctgtctac   1680
acggatggat ctggctttct cggatttgtt ggaaagttca actccactat cgttgacaag   1740
ctcaaggagt cgtctgttct gacggtcgag cccgatacca ttgtgtctct ccccgagatt   1800
cctgcttctt ctaatgccaa gcgagctatc cagactactc ccgtcactca atggggcctg   1860
tctagaatct ctcataagaa ggcccagact ggaaactacg cctacgttcg agagacagtt   1920
ggcaagcacc ccaccgtttc ttacgttgtt gactctggta tccgaaccac ccactccgag   1980
ttcggaggcc gagctgtctg gggagccaac ttcgctgaca cacagaacgc tgatcttctc   2040
ggtcacggca ctcacgttgc aggtaccgtg ggaggaaaga catacggagt cgacgccaac   2100
accaagctgg tggccgtcaa ggtgtttgca ggccgatccg cagctctctc cgtcatcaac   2160
cagggcttca cctgggctct caacgactac atctccaagc gagacactct gcctcgagga   2220
gtgctgaact tctctggagg aggacccaag tccgcttccc aggacgccct atggtctcga   2280
gctacccagg agggtctgct tgtcgccatc gctgcgggaa acgatgccgt ggacgcctgt   2340
aacgactctc ccggtaacat tggaggctcc acctctggta tcatcactgt gggttccatt   2400
gactctagcg ataagatctc cgtctggtcc ggtggacagg gatccaacta cggaacttgt   2460
gttgatgtct ttgcccccgg ctccgatatc atctctgcct cttaccagtc cgactctggt   2520
actttggtct actccggtac ctccatggcc tgtccccacg ttgccggtct tgcctcctac   2580
tacctgtcca tcaatgacga ggttctcacc cctgcccagg tcgaggctct tattactgag   2640
tccaacaccg gtgttcttcc caccaccaac ctcaagggct ctcccaacgc tgttgcctac   2700
aacggtgttg gcatttaggc aattaacaga tagtttgccg gtgataattc tcttaacctc   2760
ccacactcct ttgacataac gatttatgta acgaaactga aatttgacca gatattgttg   2820
taaatagaaa atctggcttg taggtggcaa aatgcggcgt ctttgttcat caattccctc   2880
tgtgactact cgtcatccct ttatgttcga ctgtcgtatt tcttattttc catacatatg   2940
caagtgagat gcccgtgtcc gaattc                                         2966
```

<210> SEQ ID NO 9
<211> LENGTH: 173
<212> TYPE: PRT
<213> ORGANISM: Erwinia chrysanthemi

<400> SEQUENCE: 9

```
Met Thr Glu Pro Ile Phe Met Val Gly Ala Arg Gly Cys Gly Lys Thr
1               5                   10                  15
```

```
Thr Val Gly Arg Glu Leu Ala Arg Ala Leu Gly Tyr Glu Phe Val Asp
            20                  25                  30

Thr Asp Ile Phe Met Gln His Thr Ser Gly Met Thr Val Ala Asp Val
        35                  40                  45

Val Ala Ala Glu Gly Trp Pro Gly Phe Arg Arg Arg Glu Ser Glu Ala
    50                  55                  60

Leu Gln Ala Val Ala Thr Pro Asn Arg Val Val Ala Thr Gly Gly Gly
65                  70                  75                  80

Met Val Leu Leu Glu Gln Asn Arg Gln Phe Met Arg Ala His Gly Thr
                85                  90                  95

Val Val Tyr Leu Phe Ala Pro Ala Glu Glu Leu Ala Leu Arg Leu Gln
            100                 105                 110

Ala Ser Pro Gln Ala His Gln Arg Pro Thr Leu Thr Gly Arg Pro Ile
        115                 120                 125

Ala Glu Glu Met Glu Ala Val Leu Arg Glu Arg Glu Ala Leu Tyr Gln
    130                 135                 140

Asp Val Ala His Tyr Val Val Asp Ala Thr Gln Pro Pro Ala Ala Ile
145                 150                 155                 160

Val Cys Glu Leu Met Gln Thr Met Arg Leu Pro Ala Ala
                165                 170


<210> SEQ ID NO 10
<211> LENGTH: 348
<212> TYPE: PRT
<213> ORGANISM: Escherichia coli

<400> SEQUENCE: 10

Met Glu Phe Phe Lys Lys Thr Ala Leu Ala Ala Leu Val Met Gly Phe
1               5                   10                  15

Ser Gly Ala Ala Leu Ala Leu Pro Asn Ile Thr Ile Leu Ala Thr Gly
            20                  25                  30

Gly Thr Ile Ala Gly Gly Gly Asp Ser Ala Thr Lys Ser Asn Tyr Thr
        35                  40                  45

Val Gly Lys Val Gly Val Glu Asn Leu Val Asn Ala Val Pro Gln Leu
    50                  55                  60

Lys Asp Ile Ala Asn Val Lys Gly Glu Gln Val Val Asn Ile Gly Ser
65                  70                  75                  80

Gln Asp Met Asn Asp Asn Val Trp Leu Thr Leu Ala Lys Lys Ile Asn
                85                  90                  95

Thr Asp Cys Asp Lys Thr Asp Gly Phe Val Ile Thr His Gly Thr Asp
            100                 105                 110

Thr Met Glu Glu Thr Ala Tyr Phe Leu Asp Leu Thr Val Lys Cys Asp
        115                 120                 125

Lys Pro Val Val Met Val Gly Ala Met Arg Pro Ser Thr Ser Met Ser
    130                 135                 140

Ala Asp Gly Pro Phe Asn Leu Tyr Asn Ala Val Val Thr Ala Ala Asp
145                 150                 155                 160

Lys Ala Ser Ala Asn Arg Gly Val Leu Val Val Met Asn Asp Thr Val
                165                 170                 175

Leu Asp Gly Arg Asp Val Thr Lys Thr Asn Thr Thr Asp Val Ala Thr
            180                 185                 190

Phe Lys Ser Val Asn Tyr Gly Pro Leu Gly Tyr Ile His Asn Gly Lys
        195                 200                 205

Ile Asp Tyr Gln Arg Thr Pro Ala Arg Lys His Thr Ser Asp Thr Pro
    210                 215                 220
```

```
Phe Asp Val Ser Lys Leu Asn Glu Leu Pro Lys Val Gly Ile Val Tyr
225                 230                 235                 240

Asn Tyr Ala Asn Ala Ser Asp Leu Pro Ala Lys Ala Leu Val Asp Ala
                245                 250                 255

Gly Tyr Asp Gly Ile Val Ser Ala Gly Val Gly Asn Gly Asn Leu Tyr
            260                 265                 270

Lys Ser Val Phe Asp Thr Leu Ala Thr Ala Ala Lys Thr Gly Thr Ala
        275                 280                 285

Val Val Arg Ser Ser Arg Val Pro Thr Gly Ala Thr Thr Gln Asp Ala
    290                 295                 300

Glu Val Asp Asp Ala Lys Tyr Gly Phe Val Ala Ser Gly Thr Leu Asn
305                 310                 315                 320

Pro Gln Lys Ala Arg Val Leu Leu Gln Leu Ala Leu Thr Gln Thr Lys
                325                 330                 335

Asp Pro Gln Gln Ile Gln Gln Ile Phe Asn Gln Tyr
            340                 345


<210> SEQ ID NO 11
<211> LENGTH: 109
<212> TYPE: DNA
<213> ORGANISM: Artificial sequence
<220> FEATURE:
<223> OTHER INFORMATION: Synthetic construct:  PCR fragment

<400> SEQUENCE: 11

tgcagctttc gagaaccgac gcctgggacc tgtgtctgta gggataacag ggtaattcgc     60

ttcggataac tcctgctata acgaagttat gtagggataa cagggtaat                109


<210> SEQ ID NO 12
<211> LENGTH: 98
<212> TYPE: DNA
<213> ORGANISM: Artificial sequence
<220> FEATURE:
<223> OTHER INFORMATION: Synthetic construct:  PCR fragment

<400> SEQUENCE: 12

tagggataac agggtaatta tcgcttcgga taactcctgc tatacgaagt tatgtaggga     60

taacagggta attaactata acggtcctaa ggtagcga                             98


<210> SEQ ID NO 13
<211> LENGTH: 35
<212> TYPE: DNA
<213> ORGANISM: Artificial sequence
<220> FEATURE:
<223> OTHER INFORMATION: Synthetic construct:  PCR primer

<400> SEQUENCE: 13

gatctgctag tgtataagac tctataaaaa gggcc                                35


<210> SEQ ID NO 14
<211> LENGTH: 27
<212> TYPE: DNA
<213> ORGANISM: Artificial sequence
<220> FEATURE:
<223> OTHER INFORMATION: Synthetic construct:  PCR primer

<400> SEQUENCE: 14

ctttttatag agtcttatac actagca                                         27


<210> SEQ ID NO 15
<211> LENGTH: 31
```

<212> TYPE: DNA
<213> ORGANISM: Artificial sequence
<220> FEATURE:
<223> OTHER INFORMATION: Synthetic construct: PCR primer

<400> SEQUENCE: 15
ccggaattcc tgaccagtct cacatccgac c 31

<210> SEQ ID NO 16
<211> LENGTH: 41
<212> TYPE: DNA
<213> ORGANISM: Artificial sequence
<220> FEATURE:
<223> OTHER INFORMATION: Synthetic construct: PCR primer

<400> SEQUENCE: 16
ccggaattct aaagcagata ctcaacaact cagcaatagt c 41

<210> SEQ ID NO 17
<211> LENGTH: 23
<212> TYPE: DNA
<213> ORGANISM: Artificial sequence
<220> FEATURE:
<223> OTHER INFORMATION: Synthetic construct: PCR primer

<400> SEQUENCE: 17
ggagctaccg gctccggtat cgc 23

<210> SEQ ID NO 18
<211> LENGTH: 23
<212> TYPE: DNA
<213> ORGANISM: Artificial sequence
<220> FEATURE:
<223> OTHER INFORMATION: Synthetic construct: PCR primer

<400> SEQUENCE: 18
gcgataccgg agccggtagc tcc 23

<210> SEQ ID NO 19
<211> LENGTH: 31
<212> TYPE: DNA
<213> ORGANISM: Artificial sequence
<220> FEATURE:
<223> OTHER INFORMATION: Synthetic construct: PCR primer

<400> SEQUENCE: 19
cggaaacgct ggatctttca acatcaaggc c 31

<210> SEQ ID NO 20
<211> LENGTH: 31
<212> TYPE: DNA
<213> ORGANISM: Artificial sequence
<220> FEATURE:
<223> OTHER INFORMATION: Synthetic construct: PCR primer

<400> SEQUENCE: 20
ggccttgatg ttgaaagatc cagcgtttcc g 31

<210> SEQ ID NO 21
<211> LENGTH: 26
<212> TYPE: DNA
<213> ORGANISM: Artificial sequence
<220> FEATURE:
<223> OTHER INFORMATION: Synthetic construct: PCR primer

<400> SEQUENCE: 21
ggagcaggag ttcaacaccg gtgtcg 26

<210> SEQ ID NO 22
<211> LENGTH: 26
<212> TYPE: DNA
<213> ORGANISM: Artificial sequence
<220> FEATURE:
<223> OTHER INFORMATION: Synthetic construct: PCR primer

<400> SEQUENCE: 22
cgacaccggt gttgaactcc tgctcc 26

<210> SEQ ID NO 23
<211> LENGTH: 20
<212> TYPE: DNA
<213> ORGANISM: Artificial sequence
<220> FEATURE:
<223> OTHER INFORMATION: Synthetic construct: PCR primer

<400> SEQUENCE: 23
gcagatccac tgtcaagccg 20

<210> SEQ ID NO 24
<211> LENGTH: 45
<212> TYPE: DNA
<213> ORGANISM: Artificial sequence
<220> FEATURE:
<223> OTHER INFORMATION: Synthetic construct: PCR primer

<400> SEQUENCE: 24
gctagggata aacagggtaa tgcggtagga aagagaagtt ccgcg 45

<210> SEQ ID NO 25
<211> LENGTH: 41
<212> TYPE: DNA
<213> ORGANISM: Artificial sequence
<220> FEATURE:
<223> OTHER INFORMATION: Synthetic construct: PCR primer

<400> SEQUENCE: 25
gcattaccct gttatcccta gccggactat ttccccgcag c 41

<210> SEQ ID NO 26
<211> LENGTH: 21
<212> TYPE: DNA
<213> ORGANISM: Artificial sequence
<220> FEATURE:
<223> OTHER INFORMATION: Synthetic construct: PCR primer

<400> SEQUENCE: 26
gcagccagca gcacgtagta g 21

<210> SEQ ID NO 27
<211> LENGTH: 20
<212> TYPE: DNA
<213> ORGANISM: Artificial sequence
<220> FEATURE:
<223> OTHER INFORMATION: Synthetic construct: PCR primer

<400> SEQUENCE: 27
gaatgacggg ggcaacgcag 20

<210> SEQ ID NO 28
<211> LENGTH: 25
<212> TYPE: DNA
<213> ORGANISM: Artificial sequence
<220> FEATURE:
<223> OTHER INFORMATION: Synthetic construct: PCR primer

<400> SEQUENCE: 28
cagcagccac aaatagcaga ctgcc 25

<210> SEQ ID NO 29
<211> LENGTH: 39
<212> TYPE: DNA
<213> ORGANISM: Artificial sequence
<220> FEATURE:
<223> OTHER INFORMATION: Synthetic construct: PCR primer

<400> SEQUENCE: 29
ccggaattcc gtgacaacgg atgatgctgt cacatgacg 39

<210> SEQ ID NO 30
<211> LENGTH: 37
<212> TYPE: DNA
<213> ORGANISM: Artificial sequence
<220> FEATURE:
<223> OTHER INFORMATION: Synthetic construct: PCR primer

<400> SEQUENCE: 30
ccggaattcc tgttggcatg cacagctcca ctcaacg 37

<210> SEQ ID NO 31
<211> LENGTH: 32
<212> TYPE: DNA
<213> ORGANISM: Artificial sequence
<220> FEATURE:
<223> OTHER INFORMATION: Synthetic construct: PCR primer

<400> SEQUENCE: 31
tcccgctagc cgaggtatgc aaggacgagt gc 32

<210> SEQ ID NO 32
<211> LENGTH: 48
<212> TYPE: DNA
<213> ORGANISM: Artificial sequence
<220> FEATURE:
<223> OTHER INFORMATION: Synthetic construct: PCR primer

<400> SEQUENCE: 32
ataagaatgc ggccgcgcga gctgagagcc gataccaagg gatgcgag 48

<210> SEQ ID NO 33
<211> LENGTH: 48
<212> TYPE: DNA
<213> ORGANISM: Artificial sequence
<220> FEATURE:
<223> OTHER INFORMATION: Synthetic construct: PCR primer

<400> SEQUENCE: 33
cattaccctg ttatccctac agacacaggt cccaggcgtc ggttctcg 48

<210> SEQ ID NO 34
<211> LENGTH: 77
<212> TYPE: DNA
<213> ORGANISM: Artificial sequence
<220> FEATURE:
<223> OTHER INFORMATION: Synthetic construct: PCR primer

<400> SEQUENCE: 34
ctagggataa cagggtaatt aactataacg gtcctaaggt agcgacctcg gaaaccactc 60
tgccagtcat cggtgtc 77

<210> SEQ ID NO 35
<211> LENGTH: 51
<212> TYPE: DNA
<213> ORGANISM: Artificial sequence
<220> FEATURE:
<223> OTHER INFORMATION: Synthetic construct: PCR primer

<400> SEQUENCE: 35
atagtttagc ggccgcggaa gcgtgtcaac gacatgttcc ctcttcatac c 51

<210> SEQ ID NO 36
<211> LENGTH: 35
<212> TYPE: DNA
<213> ORGANISM: Artificial sequence
<220> FEATURE:
<223> OTHER INFORMATION: Synthetic construct: PCR primer

<400> SEQUENCE: 36
cgacgataga gcaggtctca ctgttgggaa tgctg 35

<210> SEQ ID NO 37
<211> LENGTH: 35
<212> TYPE: DNA
<213> ORGANISM: Artificial sequence
<220> FEATURE:
<223> OTHER INFORMATION: Synthetic construct: PCR primer

<400> SEQUENCE: 37
ctacactgac gaagtggaca tcccggcttg gactg 35

<210> SEQ ID NO 38
<211> LENGTH: 41
<212> TYPE: DNA
<213> ORGANISM: Artificial sequence
<220> FEATURE:
<223> OTHER INFORMATION: Synthetic construct: PCR primer

<400> SEQUENCE: 38
cgcgaattcg cctgcttgaa agaagtgagt ggtatgctcg g 41

<210> SEQ ID NO 39
<211> LENGTH: 42
<212> TYPE: DNA
<213> ORGANISM: Artificial sequence
<220> FEATURE:
<223> OTHER INFORMATION: Synthetic construct: PCR primer

<400> SEQUENCE: 39
cgcgaattcc attgccacga cctgttaaaa gacaagatga cc 42

<210> SEQ ID NO 40
<211> LENGTH: 34
<212> TYPE: DNA
<213> ORGANISM: Artificial sequence
<220> FEATURE:
<223> OTHER INFORMATION: Synthetic construct: PCR primer

<400> SEQUENCE: 40
gctggccatc cgaatcctgg ctgcttacga cgcc 34

<210> SEQ ID NO 41
<211> LENGTH: 34
<212> TYPE: DNA
<213> ORGANISM: Artificial sequence
<220> FEATURE:
<223> OTHER INFORMATION: Synthetic construct: PCR primer

<400> SEQUENCE: 41
ggcgtcgtaa gcagccagga ttcggatggc cagc 34

<210> SEQ ID NO 42
<211> LENGTH: 43
<212> TYPE: DNA
<213> ORGANISM: Artificial sequence
<220> FEATURE:
<223> OTHER INFORMATION: Synthetic construct: PCR primer

<400> SEQUENCE: 42
ataagaatgc ggccgcgtgg tacgtttcgt cgcatcggac gag 43

<210> SEQ ID NO 43
<211> LENGTH: 48
<212> TYPE: DNA
<213> ORGANISM: Artificial sequence
<220> FEATURE:
<223> OTHER INFORMATION: Synthetic construct: PCR primer

<400> SEQUENCE: 43
cattaccctg ttatccctag agagctggta cttgggtatc aattgagg 48

<210> SEQ ID NO 44
<211> LENGTH: 71
<212> TYPE: DNA
<213> ORGANISM: Artificial sequence
<220> FEATURE:
<223> OTHER INFORMATION: Synthetic construct: PCR primer

<400> SEQUENCE: 44
ctagggataa cagggtaatt aactataacg gtcctaaggt agcgacctga tccaccctcc 60
tctctccaac g 71

<210> SEQ ID NO 45
<211> LENGTH: 44
<212> TYPE: DNA
<213> ORGANISM: Artificial sequence
<220> FEATURE:
<223> OTHER INFORMATION: Synthetic construct: PCR primer

<400> SEQUENCE: 45
atagtttagc ggccgcgtgg acacaaggaa gtatgcggtc gtcg 44

<210> SEQ ID NO 46
<211> LENGTH: 34
<212> TYPE: DNA
<213> ORGANISM: Artificial sequence
<220> FEATURE:
<223> OTHER INFORMATION: Synthetic construct: PCR primer

<400> SEQUENCE: 46
ctctgtcagt gttcggataa gtccttagat cacc 34

<210> SEQ ID NO 47
<211> LENGTH: 33
<212> TYPE: DNA
<213> ORGANISM: Artificial sequence
<220> FEATURE:
<223> OTHER INFORMATION: Synthetic construct: PCR primer

<400> SEQUENCE: 47
cctcacttct gtcacagatg atgcattcaa cac 33

<210> SEQ ID NO 48
<211> LENGTH: 47

```
<212> TYPE: DNA
<213> ORGANISM: Artificial sequence
<220> FEATURE:
<223> OTHER INFORMATION: Synthetic construct:  PCR primer

<400> SEQUENCE: 48

ataagaatgc ggccgcgaca ctactctggc tacagcttgc ggtactg                47


<210> SEQ ID NO 49
<211> LENGTH: 46
<212> TYPE: DNA
<213> ORGANISM: Artificial sequence
<220> FEATURE:
<223> OTHER INFORMATION: Synthetic construct:  PCR primer

<400> SEQUENCE: 49

cattaccctg ttatccctag ctcgaataac attcacaggc ttggtg                 46


<210> SEQ ID NO 50
<211> LENGTH: 75
<212> TYPE: DNA
<213> ORGANISM: Artificial sequence
<220> FEATURE:
<223> OTHER INFORMATION: Synthetic construct:  PCR primer

<400> SEQUENCE: 50

ctagggataa cagggtaatt aactataacg gtcctaaggt agcgaggtgt gtttgtagtg     60

gaggacagtg gtacg                                                   75


<210> SEQ ID NO 51
<211> LENGTH: 45
<212> TYPE: DNA
<213> ORGANISM: Artificial sequence
<220> FEATURE:
<223> OTHER INFORMATION: Synthetic construct:  PCR primer

<400> SEQUENCE: 51

atagtttagc ggccgcgtac tgaaccgact ttggtgcttg cactc                  45


<210> SEQ ID NO 52
<211> LENGTH: 33
<212> TYPE: DNA
<213> ORGANISM: Artificial sequence
<220> FEATURE:
<223> OTHER INFORMATION: Synthetic construct:  PCR primer

<400> SEQUENCE: 52

ctccacgcta atgcccatca tactctgttt ggc                               33


<210> SEQ ID NO 53
<211> LENGTH: 35
<212> TYPE: DNA
<213> ORGANISM: Artificial sequence
<220> FEATURE:
<223> OTHER INFORMATION: Synthetic construct:  PCR primer

<400> SEQUENCE: 53

cctggcgtta caaagccgag ggagacagcc ttgac                             35


<210> SEQ ID NO 54
<211> LENGTH: 48
<212> TYPE: DNA
<213> ORGANISM: Artificial sequence
<220> FEATURE:
<223> OTHER INFORMATION: Synthetic construct:  PCR primer

<400> SEQUENCE: 54
```

ataagaatgc ggccgcggtg acactgcact attggtttgc ttctgatg 48

<210> SEQ ID NO 55
<211> LENGTH: 49
<212> TYPE: DNA
<213> ORGANISM: Artificial sequence
<220> FEATURE:
<223> OTHER INFORMATION: Synthetic construct: PCR primer

<400> SEQUENCE: 55
cattaccctg ttatccctag tcgagcttcg taggagggca ttttggtgg 49

<210> SEQ ID NO 56
<211> LENGTH: 70
<212> TYPE: DNA
<213> ORGANISM: Artificial sequence
<220> FEATURE:
<223> OTHER INFORMATION: Synthetic construct: PCR primer

<400> SEQUENCE: 56
ctagggataa cagggtaatt aactataacg gtcctaaggt agcgatacgg agatgctggg 60
tacaagtagc 70

<210> SEQ ID NO 57
<211> LENGTH: 45
<212> TYPE: DNA
<213> ORGANISM: Artificial sequence
<220> FEATURE:
<223> OTHER INFORMATION: Synthetic construct: PCR primer

<400> SEQUENCE: 57
atagtttagc ggccgcctat gctacgagcg tcggattcac cacag 45

<210> SEQ ID NO 58
<211> LENGTH: 34
<212> TYPE: DNA
<213> ORGANISM: Artificial sequence
<220> FEATURE:
<223> OTHER INFORMATION: Synthetic construct: PCR primer

<400> SEQUENCE: 58
ggcacactgc tcactatcgc aggctgcaac aatg 34

<210> SEQ ID NO 59
<211> LENGTH: 36
<212> TYPE: DNA
<213> ORGANISM: Artificial sequence
<220> FEATURE:
<223> OTHER INFORMATION: Synthetic construct: PCR primer

<400> SEQUENCE: 59
cctgactcgt ctcgatactc aagacctcat tgacgc 36

<210> SEQ ID NO 60
<211> LENGTH: 31
<212> TYPE: DNA
<213> ORGANISM: Artificial sequence
<220> FEATURE:
<223> OTHER INFORMATION: Synthetic construct: PCR primer

<400> SEQUENCE: 60
ggccgctaac tataacggtc ctaaggtagc g 31

<210> SEQ ID NO 61
<211> LENGTH: 38

<212> TYPE: DNA
<213> ORGANISM: Artificial sequence
<220> FEATURE:
<223> OTHER INFORMATION: Synthetic construct: PCR primer

<400> SEQUENCE: 61
ccgaatcgat tcgctacctt aggaccgtta tagttagc 38

<210> SEQ ID NO 62
<211> LENGTH: 39
<212> TYPE: DNA
<213> ORGANISM: Artificial sequence
<220> FEATURE:
<223> OTHER INFORMATION: Synthetic construct: PCR primer

<400> SEQUENCE: 62
aatcgattcg gatcccacaa tgaagcttcc ccgcggtac 39

<210> SEQ ID NO 63
<211> LENGTH: 32
<212> TYPE: DNA
<213> ORGANISM: Artificial sequence
<220> FEATURE:
<223> OTHER INFORMATION: Synthetic construct: PCR primer

<400> SEQUENCE: 63
ctaggtaccg cggggaagct tcattgtggg at 32

<210> SEQ ID NO 64
<211> LENGTH: 72
<212> TYPE: DNA
<213> ORGANISM: Artificial sequence
<220> FEATURE:
<223> OTHER INFORMATION: Synthetic construct: PCR primer

<400> SEQUENCE: 64
tatcaaatgc ggccgcttcg ctaccttagg accgttatag ttaacacgat tcgatttgtc 60
ttagaggaac gc 72

<210> SEQ ID NO 65
<211> LENGTH: 31
<212> TYPE: DNA
<213> ORGANISM: Artificial sequence
<220> FEATURE:
<223> OTHER INFORMATION: Synthetic construct: PCR primer

<400> SEQUENCE: 65
gagtaatgct cgagtatcga agtcttgtac c 31

<210> SEQ ID NO 66
<211> LENGTH: 51
<212> TYPE: DNA
<213> ORGANISM: Artificial sequence
<220> FEATURE:
<223> OTHER INFORMATION: Synthetic construct: PCR primer

<400> SEQUENCE: 66
gcgatattac cctgttatcc ctagaatcga ttcccacaag acgaacaagt g 51

<210> SEQ ID NO 67
<211> LENGTH: 51
<212> TYPE: DNA
<213> ORGANISM: Artificial sequence
<220> FEATURE:
<223> OTHER INFORMATION: Synthetic construct: PCR primer

<400> SEQUENCE: 67
cacttgttcg tcttgtggga atcgattcta gggataacag ggtaatatcg c 51

<210> SEQ ID NO 68
<211> LENGTH: 51
<212> TYPE: DNA
<213> ORGANISM: Artificial sequence
<220> FEATURE:
<223> OTHER INFORMATION: Synthetic construct: PCR primer

<400> SEQUENCE: 68
cgcggatccc acaatgaagc tttccaccat ccttttcaca gcctgcgcta c 51

<210> SEQ ID NO 69
<211> LENGTH: 24
<212> TYPE: DNA
<213> ORGANISM: Artificial sequence
<220> FEATURE:
<223> OTHER INFORMATION: Synthetic construct: PCR primer

<400> SEQUENCE: 69
tcgcttctgg agaactgcgg cctc 24

<210> SEQ ID NO 70
<211> LENGTH: 52
<212> TYPE: DNA
<213> ORGANISM: Artificial sequence
<220> FEATURE:
<223> OTHER INFORMATION: Synthetic construct: PCR primer

<400> SEQUENCE: 70
gaggccgcag ttctgcagaa gcgagccgac aagctgccca acattgtgat tc 52

<210> SEQ ID NO 71
<211> LENGTH: 37
<212> TYPE: DNA
<213> ORGANISM: Artificial sequence
<220> FEATURE:
<223> OTHER INFORMATION: Synthetic construct: PCR primer

<400> SEQUENCE: 71
ccacctaggc tagtaggtgt ggaagtactc ctggatg 37

<210> SEQ ID NO 72
<211> LENGTH: 18
<212> TYPE: DNA
<213> ORGANISM: Artificial sequence
<220> FEATURE:
<223> OTHER INFORMATION: Synthetic construct: PCR primer

<400> SEQUENCE: 72
tactcttggt cagcccat 18

<210> SEQ ID NO 73
<211> LENGTH: 18
<212> TYPE: DNA
<213> ORGANISM: Artificial sequence
<220> FEATURE:
<223> OTHER INFORMATION: Synthetic construct: PCR primer

<400> SEQUENCE: 73
agaagggcac ttgaggga 18

<210> SEQ ID NO 74
<211> LENGTH: 17
<212> TYPE: DNA
<213> ORGANISM: Artificial sequence -continued

```
<220> FEATURE:
<223> OTHER INFORMATION: Synthetic construct:  PCR primer

<400> SEQUENCE: 74

tattgccgag cgaatgc                                                17


<210> SEQ ID NO 75
<211> LENGTH: 19
<212> TYPE: DNA
<213> ORGANISM: Artificial sequence
<220> FEATURE:
<223> OTHER INFORMATION: Synthetic construct:  PCR primer

<400> SEQUENCE: 75

cttggagatc cacatctgc                                              19


<210> SEQ ID NO 76
<211> LENGTH: 18
<212> TYPE: DNA
<213> ORGANISM: Artificial sequence
<220> FEATURE:
<223> OTHER INFORMATION: Synthetic construct:  PCR primer

<400> SEQUENCE: 76

gctgaacgac cgaattgg                                               18


<210> SEQ ID NO 77
<211> LENGTH: 17
<212> TYPE: DNA
<213> ORGANISM: Artificial sequence
<220> FEATURE:
<223> OTHER INFORMATION: Synthetic construct:  PCR primer

<400> SEQUENCE: 77

gtggtgtgca gcttgtc                                                17
```